(12) United States Patent
Hayoz

(10) Patent No.: US 6,913,712 B2
(45) Date of Patent: Jul. 5, 2005

(54) STABILIZER MIXTURE

(75) Inventor: Pascal Hayoz, Hofstetten (CH)

(73) Assignee: CIBA Specialty Chemicals Corp., Tarrytown, NY (US)

( * ) Notice: Subject to any disclaimer, the term of this patent is extended or adjusted under 35 U.S.C. 154(b) by 215 days.

(21) Appl. No.: 10/168,219

(22) PCT Filed: Dec. 14, 2000

(86) PCT No.: PCT/EP00/12734

§ 371 (c)(1),
(2), (4) Date: Jun. 19, 2002

(87) PCT Pub. No.: WO01/47900

PCT Pub. Date: Jul. 5, 2001

(65) Prior Publication Data

US 2003/0096993 A1 May 22, 2003

(30) Foreign Application Priority Data

Dec. 23, 1999 (CH) ............................................. 2368/99
Mar. 31, 2000 (CH) .............................................. 619/00

(51) Int. Cl.⁷ ..................... C08K 15/32; C08K 15/16; C08K 15/26; C08K 5/34
(52) U.S. Cl. ........................... 252/400.1; 252/400.21; 252/400.62; 252/401; 252/402; 252/403; 524/91; 524/100; 524/190; 524/359
(58) Field of Search .................... 252/400.1, 400.2, 252/400.62, 401, 402, 403, 400.21; 524/91, 100, 190, 359

(56) References Cited

U.S. PATENT DOCUMENTS

| | | | | |
|---|---|---|---|---|
| 3,113,940 A | 12/1963 | Johns et al. | ................. | 260/248 |
| 3,113,941 A | 12/1963 | Johns et al. | ................. | 260/248 |
| 3,113,942 A | 12/1963 | Johns et al. | ................. | 260/248 |
| 3,242,175 A | * 3/1966 | Duennenberger et al. | ... | 544/216 |
| 3,244,708 A | 4/1966 | Duennenberger et al. | ... | 260/248 |
| 3,249,608 A | 5/1966 | Biland et al. | ................ | 260/248 |
| 5,300,414 A | 4/1994 | Leppard et al. | ............. | 430/507 |
| 5,668,200 A | 9/1997 | Valet et al. | .................. | 524/100 |
| 6,060,543 A | 5/2000 | Bolle et al. | .................. | 524/100 |
| 6,090,370 A | * 7/2000 | Luther et al. | ................. | 424/59 |
| 6,117,997 A | 9/2000 | Bulliard et al. | ............. | 544/216 |
| 6,346,619 B1 | 2/2002 | Schäfer et al. | .............. | 544/216 |

FOREIGN PATENT DOCUMENTS

| | | |
|---|---|---|
| CH | 484695 | 3/1970 |
| DE | 19920435 | 11/1999 |
| EP | 0434608 | 6/1991 |
| EP | 0444323 | 9/1991 |
| EP | 0824909 | 2/1998 |
| GB | 975966 | 11/1964 |
| GB | 2273498 | 6/1994 |
| GB | 2319523 | 5/1998 |

* cited by examiner

*Primary Examiner*—Kriellion A. Sanders
(74) *Attorney, Agent, or Firm*—Tyler A. Stevenson

(57) ABSTRACT

Mixtures of compounds comprising a compound $G_2$ and at least one further compound from the group $G_0$, $G_1$, $G_3$, $G_4$, $G_5$, $G_6$, the compounds $G_0$–$G_6$ corresponding to formula (I) in which, in the compound $G_0$, the radicals $R_1$, $R_2$, $R_3$, $R_4$, $R_5$ and $R_6$ are each hydrogen; $G_1$, the radical $R_1$ is Q and $R_2$, $R_3$, $R_4$, $R_5$ and $R_6$ are each hydrogen; $G_2$, the radicals $R_1$ and $R_2$ independently of one another are each Q and $R_3$, $R_4$, $R_5$ and $R_6$ are each hydrogen; $G_3$ the radicals $R_1$, $R_2$ and $R_3$ independently of one another are each Q and $R_4$, $R_5$ and $R_6$ are each hydrogen; $G_4$, the radicals $R_1$, $R_2$, $R_3$ and $R_4$ independently of one another are each Q and $R_5$ and $R_6$ are each hydrogen; $G_5$, the radicals $R_1$, $R_2$, $R_3$, $R_4$ and $R_5$ independently of one another are each Q and $R_6$ is hydrogen; $G_6$, the radicals $R_1$, $R_2$, $R_3$, $R_4$, $R_5$ and $R_6$ independently of one another are each Q; and Q and the other symbols are as defined in claim 1, are effective as stabilizers for organic material with respect to damaging exposure to light, oxygen and/or heat.

13 Claims, No Drawings

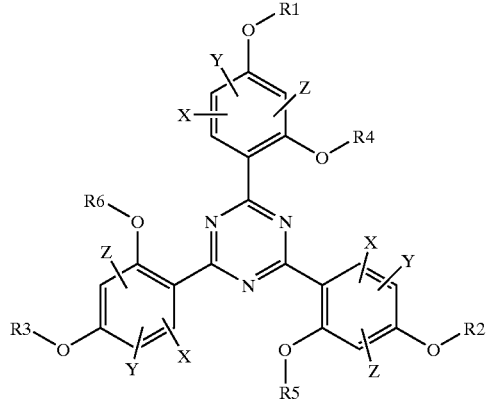

STABILIZER MIXTURE

The present invention relates to a stabilizer comprising a mixture of 2,4,6-tris(2,4-dihydroxyphenyl)-1,3,5-triazines with at least 2 types of individual compounds, namely those in which 2 of the 6 hydroxyl groups have been replaced by a hydrocarbyloxy radical, and at least one further type in which fewer and/or more than 2 of the 6 hydroxyl groups have been replaced by a hydrocarbyloxy radical. The invention likewise relates to its use for stabilizing organic material, to a corresponding composition and method for stabilizing organic material, and to individual novel compounds.

Individual compounds of the hydroxyphenyltriazine type which are derived from 2,4,6-tris(2,4-diphenyl)1,3,5-triazine and their use as stabilizers are described, inter alia, in GB-A-975966, U.S. Pat. No. 3,113,940, U.S. Pat. No. 3,113,941, U.S. Pat. No. 3,113,942, CH-A-467833, U.S. Pat. No. 3,244,708, U.S. Pat. No. 3,249,608, EP-A-434608, U.S. Pat. No. 5,300,414, U.S. Pat. No. 5,489,503, GB-A-2319523, GB-A-2337049, CH-A484695.

Certain mixtures of hydroxyphenyltriazines have also already been proposed as stabilizers, for example in EP-A-444323, GB-A-2317893, U.S. Pat. No. 5,668,200.

Mixtures of compounds have now been found which possess surprisingly advantageous properties. The invention therefore firstly provides a mixture comprising a compound $G_2$ and at least one further compound from the group $G_0$, $G_1$, $G_3$, $G_4$, $G_5$, $G_6$, the compounds $G_8$–$G_8$ each corresponding to the formula I

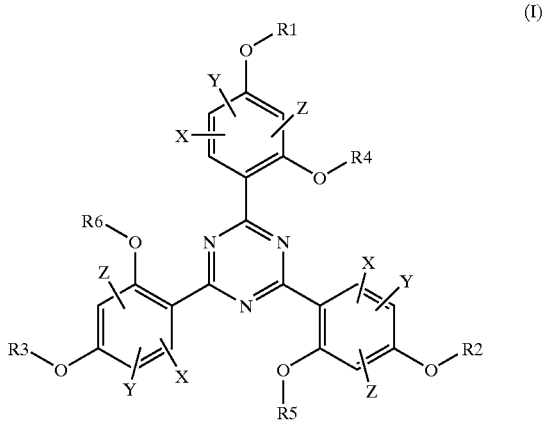

(I)

in which
X, Y and Z independently of one another are H, $T_1$, $OT_1$, $NT_1T_2$, $ST_1$, $SOT_1$, $SO_2T_1$, $SO_2NT_1T_2$, $SO_3H$, $SO_3T_1$, $SO_3M$ or -D; where
$T_1$ and $T_2$ are $C_1$–$C_{50}$alkyl, $C_5$–$C_{12}$cycloalkyl, $C_7$–$C_{18}$arylalkyl, $C_7$–$C_{18}$alkylaryl, $C_6$–$C_{18}$aryl, $C_2$–$C_{50}$alkenyl, $C_5$–$C_{12}$cycloalkeny, $C_2$–$C_{50}$cycloalkynyl, $C_5$–$C_{12}$bicycloalkynyl, $C_5$–$C_{18}$bicycloalkyl, $C_6$–$C_{18}$bicycloalkenyl; or one of these radicals substituted by one or more D and/or, if desired, interrupted by one or more units E;
D is selected from —R, —OH, —OR, —SR, —NRR', —NRSO$_2$R$_1$, —SOR, —SO$_2$R, —SO$_2$NRR', —SO$_3$H, —SO$_3$M, —SO$_3$R, oxiranyl, -Hal, —CN, —COR, —COOR, —COOM, —CONRR', —OCOR, —OCOOR, —OCONRR', —NRCOR', —NRCOOR', —NRCONR'R";
E is selected from —O—, —S—, —NR—, —SO—, —SO$_2$—, —SO$_2$NR—, —CO—, —COO—, —CONR—, —OCO—, —O——CO—O—, OCONR—, —NRCO—, —NRCO—O— and —NRCONR'—;
R, R', R", R* independently of one another are H, $C_1$–$C_{50}$alkyl, $c_5$–$C_{12}$cycloalkyl, $C_7$–$C_{18}$arylalkyl, $C_7$–$C_{18}$alkylaryl, $C_6$–$C_{18}$aryl, $C_2$–$C_{50}$alkenyl, $C_5$–$C_{12}$cycloalkenyl, $C_2$–$C_{50}$alkynyl, $C_5$–$C_{12}$cycloalkynyl, $C_5$–$C_{18}$bicycloalkyl, $C_6$–$C_{18}$bicycloalkenyl; or are one of these aforementioned hydrocarbon radicals substituted by OH and/or interrupted by O;
Hal is —F, —Cl, —Br or —I;
M is a monovalent metal cation, preferably an alkali metal cation, or is N(RR'R"R*)$^+$, especially ammonium, or is P(RR'R"R*)$^+$:
and in which, in the compound
$G_0$, the radicals $R_1$, $R_2$, $R_3$, $R_4$, $R_5$ and $R_6$ are each hydrogen;
$G_1$, one radical from the group $R_1$, $R_2$, $R_3$, $R_4$, $R_5$ and $R_6$ is Q and the others are each hydrogen;
$G_2$, two radicals from the group $R_1$, $R_2$, $R_3$, $R_4$, $R_5$ and $R_6$ are each Q and the others are each hydrogen;
$G_3$, three radicals from the group $R_1$, $R_2$, $R_3$, $R_4$, $R_5$ and $R_6$ are each Q and the others are each hydrogen;
$G_4$, four radicals from the group $R_1$, $R_2$, $R_3$, $R_4$, $R_5$ and $R_6$ are each Q and the others are each hydrogen;
$G_5$, five radicals from the group $R_1$, $R_2$, $R_3$, $R_4$, $R_5$ and $R_6$ are each Q and 1 radical is hydrogen;
$G_6$, the radicals $R_1$, $A_2$, $R_3$, $R_4$, $R_5$ and $R_6$ are each 0; and
Q is —$T_1$, —$COT_1$, —$COH_1$, —$COOT_1$, —$CONHT_1$, —$CONH_2$ or —$CONT_1T_2$.

Preferred mixtures are those in which, in the compound
$G_0$, the radicals $R_1$, $R_2$, $R_3$, $R_4$, $R_5$ and $R_6$ are each hydrogen;
$G_1$, the radical $R_1$ is Q and $R_2$, $R_3$, $R_4$, $R_5$ and $R_6$ are each hydrogen;
$G_2$, the radicals $R_1$ and $R_2$ independently of one another are each Q and $R_3$, $R_4$, $R_5$ and $R_6$ are each hydrogen;
$G_3$, the radicals $R_1$, $R_2$ and $R_3$ independently of one another are each Q and $R_4$, $R_5$ and $R_5$ are each hydrogen;
$G_4$, the radicals $R_1$, $R_2$, $R_3$ and $R_4$ independently of one another are each Q and $R_5$ and $R_6$ are each hydrogen;
$G_5$, the radicals $R_1$, $R_2$, $R_3$, $R_4$ and $R_5$ independently of one another are each Q and $R_6$ is hydrogen; and
$G_6$, the radicals $R_1$, $R_2$, $R_3$, $R_4$, $R_5$ and $R_6$ independently of one another are each Q.

$C_1$–$C_{50}$alkyl, for example $T_1$, $T_2$, R, R', R* or R", is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methyl-undecyl, dodecyl, 1,1,3,3,5,5-hexamethylhexyl, tridecyl, tetradecyl, pentadecyl, hexadecyl, heptadecyl, octadecyl, eicosyl, docosyl. One of the preferred definitions is for example $C_2$–$C_{18}$alkyl. A particularly preferred definition of R, R' and R" is $C_1$–$C_4$alkyl.

$T_1$, $T_2$, R, R', R* and R" as $C_5$–$C_{12}$cycloalkyl are for example cyclopentyl, cyclohexyl, cycloheptyl, cyclooctyl, cyclononyl, cyclodecyl, cyclododecyl. Cyclohexyl and cyclododecyl are preferred.

$T_1$, $T_2$, R, R', R* and R" as $C_7$–$C_{18}$arylalkyl are for example benzyl, methylbenzyl, cumyl.

$T_1$, $T_2$, R, R', R* and R" as $C_7$–$C_{18}$alkylaryl are for example methylphenyl, dimethylphenyl, mesityl, ethylphenyl, propylphenyl, butylphenyl, dibutylphenyl, pentylphenyl, hexylphenyl, heptylphenyl, octylphenyl.

$T_1$, $T_2$, R, R', R* and R" as $C_6$–$C_{18}$aryl are for example phenyl, naphthyl, biphenylyl. Phenyl is preferred.

$T_1, T_2, R, R', R^*$ and $R''$ as $C_2–C_{50}$alkenyl are for example vinyl, allyl, butenyl, pentenyl, hexenyl, heptenyl, octenyl; preference is given to allyl if the radical binds to a heteroatom (an atom other than carbon. e.g. O), and vinyl where the radical binds to carbon.

A preferred definition of D as OCOR is acryloyloxy or methacryloyloxy.

$T_1, T_2, R, R', R^*$ and $R''$ as $C_5–C_{12}$cycloalkenyl is preferably cyclohexenyl.

$T_1, T_2, R, R', R^*$ and $R''$ as $C_2–C_{50}$alkynyl is preferably propargyl.

$T_1, T_2, R, R', R^*$ and $R''$ as $C_5–C_{12}$cycloalkynyl is for example cyclohexynyl.

$T_1, T_2, R, R', R^*$ and $R''$ as $C_5C_{18}$bicycloalkyl is for example bicyclo[2.2.1]heptyl, bicyclo[2.2.2]octyl (norbornyl).

$T_1, T_2, R, R', R^*$ and $R''$ as $C_6–C_{18}$bicycloalkenyl is for example bicyclo[2.2.1]hept-2-enyl, bicyclo[2.2.2]octenyl (norbornenyl).

Oxiranyl is an epoxy radical of the formula

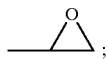

it is preferably attached to $CH_2$ and so forms a glycidyl radical.

As described above, the aforementioned radicals may be substituted by D and/or, if desired, interrupted by E. Interruptions are of course possible only in the case of radicals containing at least 2 carbon atoms connected to one another by single bonds; $C_6–C_{18}$aryl is not interrupted; interrupted arylalkyl or alkylaryl contains the unit E in the alkyl moiety.

$D_1$ are carbon-bonding substituents D: —R, —CN, —COR, —COOR, —COOM, —CONRR'; D are heteroatom-bonding substituents D: —OH, —OR, —SR, —NRR', —NRSO$_2$R', —SOR, —SO$_2$R, —SO$_2$NRR', —SO$_3$H, —SAM, -Hal, —OCOR, OCOOR, —OCONRR', —NRCOR', NRCOOR', —NRCONR'R".

$D_2$-substituted acyclic radicals contain preferably 2 or more, especially 2–18, carbon atoms. $D_2$ is generally not attached in the α position.

Acyclic radicals, where interrupted, contain preferably 3 or more, especially 318, carbon atoms. In general, $T_1$ or $T_2$ as interrupted radicals contain 2 or more carbon atoms for each interrupting unit E. In general, not more than 1 interrupting unit E is inserted into a C—C single bond, avoiding accumulations of the type —E—E—. Asymmetric E may be present in any position; for example, E as —CO—O— embraces both esters (in which —CO is aligned facing the molecule core) and retroesters (in which —O— is aligned facing the molecule core).

Hal is for example fluorine, chlorine or bromine or iodine. Chlorine is preferred.

Alkyl is for example $C_1–C_{18}$alkyl like methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl or octadecyl. Cycloalkyl is mainly $C_5–C_{12}$ cycloalkyl like cyclopentyl, cyclohexyl, cycloheptyl, cyclooctyl or cyclododecyl. Alkenyl stands within the definitions given inter alia for vinyl, allyl, 1- or 2-butenyl etc. The residues defined, where appropriate, may be straight or branched chain. Polyvalent residues are derived from the corresponding monovalent residues by abstraction of a H-atom; thus, $C_1–C_{18}$alkenylen stands, for example, for methylene, ethylene, ethylidene, 1,1-, 1,2- or α,ω-propylene, or the corresponding butylene, pentylene, hexylene, heptylene, octylene etc. isomers.

$T_1$ or $T_2$ as $C_1–C_{50}$alkyl substituted by one or more D and/or interrupted by one or more units E are for example $(CH_2CH_2O)_n$—$R_x$, where n is a number from the range 1–20 and $R_x$ is H or $C_1–C_{10}$alkyl or $C_2–C_{10}$alkanoyl (e.g. CO—CH($C_2H_5$)$C_4H_9$),
$CH_2$—CH(O$R_y$')—$CH_2$—O-$R_y$, where $R_y$ is $C_1–C_{18}$alkyl, $C_5–C_{12}$cycloalkyl, phenyl, $C_7–C_{15}$phenylalkyl, and $R_y$' embraces the same definitions as $R_y$ or is H;
$C_1–C_8$alkylene-COO—$R_1$, e.g. $CH_2$COOR, CH($CH_3$) COOR$_2$, C($CH_3$)$_2$COOR$_2$, where $R_2$ is H, $C_1–C_{18}$alkyl, $(CH_2CH_2)_{1-15}$-$R_x$ and $R_x$ embraces the definitions indicated above;
$C_1–C_{12}$alkylene-SO$_3$H; $CH_2CH_2$—O—CO—CH=CH$_2$; $CH_2CH(OH)CH_2$—O—CO—C(CH$_3$)=CH$_2$.

$T_1$ and $T_2$ are preferably, independently of one another, $C_1–C_{18}$alkyl, $C_5–C_{1-2}$cycloalkyl, $C_7–C_{18}$-phenylalkyl, $C_7–C_{18}$alkylphenyl, phenyl, naphthyl, biphenylyl, $C_2–C_{18}$alkenyl, $C_5–C_{12}$-cycloalkenyl, $C_2–C_{12}$ alkynyl; or are $C_1–C_{18}$alkyl, $C_5–C_{12}$cycloalkyl, $C_7–C_{18}$phenylalkyl, $C_7–C_{18}$-alkylphenyl, phenyl, naphthyl, biphenylyl, $C_2–C_{18}$alkenyl, $C_5–C_{12}$cycloalkenyl, $C_2–C_{12}$alkynyl in each case substituted by one or more D; or are $C_2–C_{50}$alkyl, $C_7–C_{18}$phenylalkyl, $C_7–C_{18}$alkylphenyl or $C_7–C_{18}$alkenyl interrupted by one or more E; or are $C_3–C_{50}$alkyl or $C_4–C_{18}$alkenyl or $C_7–C_{18}$-phenylalkyl which is substituted by D and interrupted by E; especially $C_1–C_{18}$lalkyl, $C_5–C_{12}$cycloalkyl, $C_7–C_{18}$phenylalkyl, $C_7–C_{18}$alkylphenyl, phenyl, naphthyl, biphenylyl, $C_2–C_{18}$alkenyl, cyclohexenyl; or $C_1–C_{18}$alkyl, cyclohexyl, cyclododecyl, $C_7–C_{18}$phenylalkyl, $C_7–C_{18}$alkylphenyl, phenyl, naphthyl, biphenylyl, $C_2–C_{18}$alkenyl or cyclohexenyl in each case substituted by one or more D; or $C_2–C_{50}$alkyl, $C_7–C_{18}$phenylalkyl, $C_7C_{18}$alkylphenyl or $C_4–C_{18}$alkenyl interrupted by one or more E; or are $C_3C_{50}$alkyl or $C_4–C_{18}$alkenyl or $C_7–C_{18}$phenylalkyl which are substituted by D and interrupted by E.

Substituted cycloalkyl is for example methylcyclopentyl, dimethylcyclopentyl, methylcyclo-hexyl, hydroxycyclohexyl, carboxycyclohexyl, alkoxycarbonylcyclohexyl, dimethylcyclohexyl, trimethylcyclohexyl, tert-butylcyclohexyl.

M as monovalent metal cation may also be a positively charged metal complex; it is preferably an alkali metal cation, for example of the metals U, Na, K, Cs; in particular Na. M as $N(R)_4$+is preferably ammonium $(NH_4)^+$.

X, Y and Z in preferred mixtures are each hydrogen, -$T_1$ or D, especially H.

A group of compounds of the formula I of particular technical interest is that in which X, Y and Z are each hydrogen and Q has the definition $T_1$.

Of particular significance is a mixture of compounds in which $G_2$ and a further compound from the group $G_0$, $G_1$, $G_3$, $G_4$, $G_5$, $G_6$ are each present in an amount of from 1 to 99 parts by weight, for example 1–90 or 1–80 parts by weight, especially 5–80 parts by weight, based in each case on 100 parts by weight of the total compounds $G_0$–$G_6$ present in the mixture.

Preferred mixtures of compounds comprise, besides $G_2$, 2 further compounds from the group $G_0$–$G_6$, especially $G_2$, $G_3$ and $G_4$, each in an amount of from 1 to 98 parts by weight, based on 100 parts by weight of the total compounds present in the mixture. Mixtures of compounds which are likewise preferred comprise Go, $G_1$ and $G_2$, or, with particular preference, $G_1$, $G_2$ and $G_3$ each in an amount of from 1 to 98 parts by weight, based on 100 parts by weight of the total compounds present in the mixture. Particularly preferred mixtures of compounds comprise, besides $G_2$, 3 further compounds from the group $G_8$–$G_0$, for example $G_1$, $G_2$, $G_3$ and $G_4$, especially $G_1$, $G_2$, $G_3$, $G_4$ and $G_5$, each in an amount of from 1 to 97 parts by weight, based on 100 parts by weight of the total compounds present in the mixture. Proportions of the individual compounds which are of particular interest are in each case 1-90, especially 1–80 parts by weight, in particular 580 parts by weight, based on 100 parts by weight of the total compounds $G_0$–$G_6$ present in the mixture.

Preferred components of the mixture of compounds of the invention are those in which X, Y and Z independently of one another are —H, —$T_1$, or D;

$T_1$ and $T_2$ independently of one another are $C_1$–$C_{18}$alkyl, $C_5$–$C_{12}$cycloalkyl, $C_7$–$C_{18}$phenylalkyl, $C_7$–$C_{18}$alkylphenyl, phenyl, naphthyl, biphenylyl, $C_2C_{18}$alkenyl, $C_5$–$C_{12}$cycloalkenyl, $C_2$–$C_{12}$-alkynyl; or are $C_1$–$C_{18}$alkyl, $C_5$–$C_{12}$cycloalkyl, $C_7$–$C_{18}$phenylalkyl, $C_7$–$C_{18}$alkylphenyl, phenyl, naphthyl, biphenylyl, $C_2$–$C_{18}$alkenyl, $C_5$–$C_{12}$cycloalkenyl, $C_2$–$C_{12}$alkynyl in each case substituted by one or more D; or are $C_2$–$C_{50}$alkyl, $C_7$–$C_{18}$phenylalkyl, $C_7$–$C_{18}$alkylphenyl, $C_5$–$C_{12}$-cycloalkyl, $C_5$–$C_{12}$cycloalkenyl or $C_4$–$C_{18}$alkenyl in each case interrupted by one or more E; or are $C_2$–$C_{50}$alkyl, $C_3$–$C_{18}$alkenyl, $C_7$–$C_{18}$alkylphenyl, $C_5$–$C_{12}$cycloalkyl, $C_5$ $C_{12}$cycloalkenyl or $C_7C_{18}$phenylalkyl which are substituted by D and interrupted by E;

D is —R, —OH, —OR, —NRR', -Hal, —CN, —COR, —COOR, —COOM, —CONRR', —OCOR, —OCOOR, —OCONRR', —NRCOR', —NRCOOR', —NRCONR'R", oxiranyl, —$SO_3H$, —$SO_3M$;

E is —O—, —NR—, —CO—, COO—, —CONR—, —OCO—, —OCOO—, OCONR—, —NRCO—, —NRCOO—, —NRCONR'—;

R, R', R", R* Independently of one another are H, $C_1$–$C_{50}$alkyl, $C_5$–$C_{12}$cycloalkyl, $C_7$–$C_{18}$ phenylalkyl, $C_7$–$C_{18}$alkylphenyl, phenyl, naphthyl, biphenylyl, $C_2$–$C_{50}$alkenyl, $C_5$–$C_{12}$-cycloalkenyl, $C_2$–$C_{50}$alkynyl;

Hal is —F or —Cl; and

M is an alkali metal cation or N(RR'R"R*).

$T_1$, $T_2$ and also R, R', R* and R" may independently of one another be straight-chain or branched.

Particularly preferred components of the mixture of compounds of the invention are those in which Q is —Ts, —COT, or —$CONT_1T_2$;

X, Y and Z independently of one another are —H, —$T_1$, D;

D is —R, —OH, —OR, -Hal, —COR, —COOR, —COOM, —CONRR', —OCOR, —OCOOR, —OCONRR', —$SO_3H$, —$SO_3M$;

E is 4, —C, —COO—, —CONR—, —OCO—, —OCO—, OCONR—;

R R', R" independently of one another are H, $C_1$–$C_{18}$alkyl, cyclohexyl, cyclododecyl, $C_7$–$C_{18}$phenylalkyl, $C_7$–$C_{18}$alkylphenyl, phenyl, $C_2$–$C_{12}$alkenyl; and Hal is —F or —Cl; and M is Li, Na or K.

Compounds of the mixture of compounds of the invention that are preferred in particular are those in which Q is —$T_1$, —$COT_1$, —$CONT_1T_2$;

X, Y and Z independently of one another are —H, —$T_1$ or —D;

$T_1$ and $T_2$ independently of one another are $C_1$–$C_{18}$alkyl, $C_5$–$C_{12}$cycloalkyl, $C_7$–$C_{18}$phenylalkyl, $C_7$–$C_{18}$alkylphenyl, phenyl, naphthyl, biphenylyl, $C_2$–$C_{18}$alkenyl; or are $C_1$–$C_{1-8}$alkyl, cyclohexyl, $C_7$–$C_{18}$phenylalkyl, $C_7$–$C_{18}$alkylphenyl, phenyl, $C_3$–$C_{12}$alkenyl in each case substituted by D; or are $C_3$–$C_{50}$alkyl, $C_7$–$C_{18}$phenylalkyl, $C_7$–$C_{18}$alkylphenyl or $C_4$–$C_{18}$alkenyl interrupted by E; or are $C_2$–$C_{50}$alkyl or $C_4$–$C_{18}$alkenyl or $C_7$–$C_{18}$phenylalkyl which are substituted by D and interrupted by E;

D is —R, —OH, —OR, -Hal, —COR", COOR, —COOM, —OCOR", —$SO_3H$, —$SO_3M$;

E is —O—, —CO—, —COO—, —OCO—;

R is H, $C_1$–$C_{18}$alkyl, cyclohexyl, $C_7$–$C_{18}$phenylalkyl, $C_7$–$C_{18}$alkylphenyl, phenyl, $C_3$–$C_{12}$alkenyl;

R" is H, $C_1$–$C_{18}$alkyl, cyclohexyl, $C_7$–$C_{18}$phenylalkyl, $C_7$–$C_{18}$alkylphenyl, phenyl, $C_3C_{12}$alkenyl;

Hal is —F or —Cl; and

M is Li, Na or K, especially those in which

Q is —$T_1$; X, Y and Z independently of one another are —H, $C_1$–$C_{12}$alkyl, $C_7$–$C_9$phenylalkyl or $C_3$–$C_6$alkenyl; and $T_1$ and $T_2$ independently of one another are $C_1$–$C_{18}$alkyl, $C_5$–$C_{12}$cycloalky, $C_7$–$C_{18}$phenylalkyl, $C_7$–$C_{18}$alkylphenyl, phenyl, naphthyl, biphenylyl, $C_2$–$C_{18}$alkenyl; or are $C_1$–$C_{18}$alkyl, cyclohexyl, $C_7C_{18}$phenylalkyl, $C_7$–$C_{18}$alkylphenyl, phenyl, $C_3$–$C_{12}$alkenyl in each case substituted by D.

Components $G_0$–$G_8$ of the mixture of compounds of the invention may be prepared by known methods or in analogy to such methods. Such methods are described, for example, in GB-A-975966, CH-A484695. The compounds of the formula I may also be prepared in analogy to one of the methods specified in EP-A-434608, one of the publications mentioned at the outset, or in the publication by H. Brunetti and C. E. Luthi, Helv. Chim. Acta 55, 1566 (1972). The starting point is oloudiciously the compound 2,4,6tris(2,4-dihydroxyphenyl)1,3,5-triazine (trisresorcinoltriazine) or an appropriately substituted derivative of this compound ($G_0$, starting compound of the formula II). The starting compound of formula II

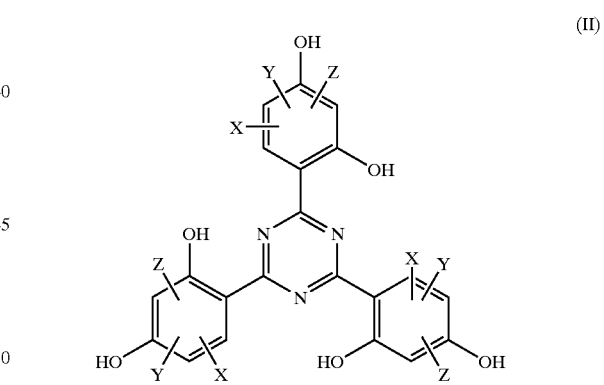

(II)

may be prepared, for example, in analogy to EP-A-165608 by means of Friedel-Crafts Reaction of cyanuric chloride or cyanuric halide and the corresponding resorcinol derivatives (which already contain substituents X, Y and Z), X, Y and Z being as defined above.

Unsubstituted trisresorcinoltriazine may also be substituted subsequently by introducing the groups X, Y and Z.

The starting compound of the formula II may be reacted further in accordance with known methods to give compounds $G_1$–$G_6$ of formula I; such reactions and methods are described, for example, in EP-A-434 608, page 15, line 11, to page 17, line 1. Where organic halides Hal-Q or sulfonates $Ts$-$SO_3$-Q in which Hal is a halogen atom and Ts is for example 4-tosyl or methyl are used for reaction with the free phenolic OH of the compound $G_0$, the reaction is oudiciously conducted in the presence of an acid binding agent and an appropriate solvent. The use of aprolic solvents such as diglyme for example is advantageous. Preference is given to the solvents dimethyl sulfoxide, dimethylformamide (DMF), dimethylacetamide, acetone, ethyl methyl ketone, ethanol, methanol, isopropanol, diglyme, water, toluene, xylene, and mixtures thereof. Established acid binding agents include bases such as carbonates and bicarbonates or alkoxides, such as $Na_2CO_3$, $K_2CO_3$, Na ethoxide, Na methoxide or potassium tert-butoxide, or metal hydrides. The products may be worked up in conventional manner, for example by separating off the solvent and/or carrying out crystallization and/or distillation.

Alternatively, cyanuric chloride or cyanuric halide may be reacted with 3 equivalents of a resorcinol derivative of the formula

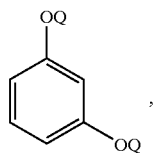

for example In analogy to EP-A-165608, to give $G_6$ which can subsequently be reacted further by cleaving some of the bonds O–Q (e.g. dealkylation by means of $AlCl_3$) to give compounds of the type $G_0$–$G_5$ or of the mixture of the invention.

The stabilizer of the invention may subsequently be obtained by mixing a compound of the type $G_2$ of formula I with at least one further compound of type $G_0$, $G_1$ and/or $G_3$–$G_8$ as described earlier on above.

It is particularly advantageous to direct the alkylation or acylation step in such a way that the desired mixture is formed starting from compounds of the formula II. This is the preferred route for preparing mixtures of the formula II. For this purpose, the abovementioned starting compound of the formula II is judiciously reacted as described with Hal-Q, advantageously in the presence of a base (e.g. carbonates or hydroxides of alkali metals or alkaline earth metals such as Na, K, Ca, or ammonia or amines such as triethylamine, dibutylamine or tributylamine, etc.) and of appropriate solvent, examples being those described above; particularly preferred solvents are dimethylformamide (DMF), dimethylacetamide, N-methylpyrrolidone. Besides this solvent it is also possible to use a cosolvent, advantageously selected from aliphatic or aromatic hydrocarbons, esters or ketones, such as heptane, benzene, toluene, xylene, butyl acetate, ethyl acetate, ethyl methyl ketone, methyl isobutyl ketone. For the reaction, it is preferred to carry out heating with stirring, for example at 40–200° C., in particular at 80–150° C., often for a duration of 1–10 h, especially 2–8h. The desired degree of reaction is judiciously monitored by means of customary analytical methods, such as thin layer chromatography (TLC) or high performance liquid chromatography (HPLC), and the reaction is terminated when the desired degree of reaction is reached, termination being effective, for example, by temperature reduction, addition of water, and/or neutralization. It is possible for further reaction steps to follow, examples being transesterification, saponification, salt formation, esterification, etherification. The mixture of compounds of the invention is subsequently obtained, usually following removal of salts and/or solvent(s), in some cases following extraction of the aqueous mixture with an appropriate organic solvent. Appropriate extractants in turn are the substances listed above as possible cosolvents. An advantage of this method is that the product thus obtained can generally be used as a stabilizer without further purification. It is also possible to use the mixture obtained directly from the synthesis.

In certain cases a downstream purification step may also be of advantage: for example, the filtration of the solution of the mixture of products, judiciously originating from the extraction, over a filter aid (e.g. magnesium sulfate, sodium sulfate, aluminium oxide, clay, activated carbon, silica gel, etc.), especially when an improvement in colour or lightening of the product mixture is desired. Distillation, precipitation and recrystallization are likewise possible for purification.

Certain constituents of the mixture of the invention are novel compounds. The invention therefore additionally provides compounds of the type $G_1$, $G_2$, $G_3$, $G_4$, $G_5$ and $G_6$ of the formula III

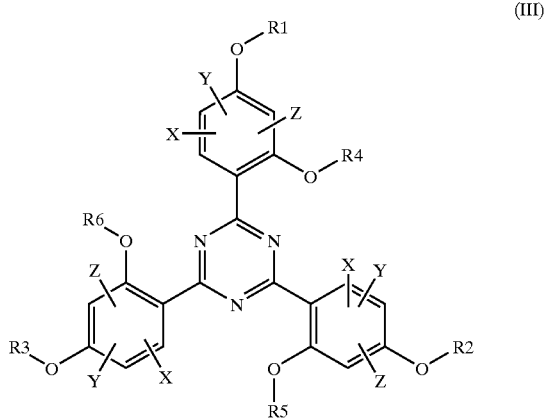

in which
X, Y and Z independently of one another are H, $T_1$, $OT_1$, $NT_1T_2$, $ST_1$, $SOT_1$, $SO_2T_1$, $SO_2NT_1T_2$, $SO_3H$, $SO_3T_1$, $SO_3M$ or —D; where $T_1$ and $T_2$ are $C_1$–$C_{50}$alkyl, $C_5$–$C_{12}$cycloalkyl, $C_7$–$C_{18}$arylalkyl, $_7$—$C_{18}$alkylaryl, $C_6$–$C_{18}$aryl, $C_2$–$C_{50}$alkenyl, $C_5$–$C_{12}$cycloalkenyl, $C_2$–$C_{50}$alkynyl, $C_5$–$C_{12}$cycloalkynyl, $C_5$–$C_{18}$bicycloalkyl, $C_6$–$C_{18}$bicycloalkenyl; or one of these radicals substituted by one or more D and/or, if desired, interrupted by one or more units E;

$T_3$ is $C_1$–$C_{50}$alkyl, $C_2$–$C_{50}$alkenyl, $C_2$–$C_{50}$alkynyl; or $C_1$–$C_{50}$alkyl, $C_5$–$C_{12}$cycloalkyl, $C_7$–$C_{18}$arylalkyl, $C_7$–$C_{18}$alkylaryl, $C_6$—$C_{18}$aryl, $C_2$–$C_{50}$alkenyl, $C_5$–$C_{12}$cycloalkenyl, $C_7$–$C_{50}$alkynyl, $C_5$–$C_{12}$cycloalkynyl, $C_5$–$C_{18}$bicycloalkyl, $C_6$–$C_{18}$bicycloalkenyl in each case substituted by one or more —SOR, —$SO_2R$, —$SO_2NRR'$, —$SO_3H$, —$SO_3M$, —COR, —COOR, —COOM, —CONRR', —OCOR, —OCOOR, —OCONRR', —NRCOR' —NRCOOR', —NRCONR'R";

$T_4$ is $C_1$–$C_{50}$alkyl, $C_5$–$C_{12}$cycloalkyl, $C_7$–$C_{18}$arylalkyl, $C_7$–$C_{18}$alkylaryl, $C_5$–$C_{18}$aryl, $C_2$–$C_{60}$alkenyl, $C_5$–$C_{12}$cycloalkenyl, $C_2$–$C_{50}$alkynyl, $C_5$–$C_{12}$cycloalkynyl, $C_5$–$C_{18}$bicycloalkyl, $C_6$–$C_{18}$bicycloalkenyl in each case substituted by one or more —COOM and, if desired, interrupted by one or more units E and/or substituted by D;

D is selected from —R, —OH, —OR, —SR, —NRR', —$NRSO_2R'$, —SOR, —$SO_2R$, —$SO_2NRR'$, —$SO_3H$, —$SO_3M$, -Hal, —CN, —COR, —COOR, —COOM, —CONRR', 4COR, —OCOOR, —OCONRR', —NRCOR', —NRCOOR', —NRCONR'R";

E is selected from —O—, —S—, —NR—, —SO—, —SO$_2$, SO$_2$NR—, —CO—, —COO—, —CONR—, —OCO—, —O—COO—, OCONR—, —NRCO—, —NR—COO— and —NRCONR'—;

R, R', R" independently of one another are H, C$_1$–C$_{50}$alkyl, C$_5$–C$_{12}$cycloalkyl, C$_7$–C$_{18}$arylalkyl, C$_7$–C$_{18}$alkylaryl, C$_6$–C$_{18}$aryl, C$_2$–C$_{50}$alkenyl, C$_5$–C$_{12}$cycloalkenyl, C$_2$–C$_{50}$alkynyl, C$_5$–C$_{12}$cycloalkynyl, C$_5$–C$_{18}$bicycloalkyl, C$_6$–C$_{18}$bicycloalkenyl;

Hal is —F, —Cl, —Br or —I;

M is a monovalent metal cation, preferably an alkali metal cation, or is N(RR'R"R*)$^+$, especially ammonium, or is P(RR'R" R*)$^+$;

and in which, in the compound

G$_1$, the radical R$_1$ is Q$_1$ and R$_2$, R$_3$, R$_4$, R$_5$ and R$_8$ are each hydrogen;

G$_2$, the radicals R$_1$ and R$_2$ independently of one another are each Q$_2$ and R$_3$, R$_4$, R$_5$ and R$_5$ are each hydrogen;

G$_3$, the radicals R$_1$, R$_2$, and R$_3$ independently of one another are each Q$_3$ and R$_4$, R$_5$ and R$_5$ are each hydrogen;

G$_4$, the radicals R$_1$, R$_2$, R$_3$ and R$_4$ independently of one another are each Q$_3$ and R$_5$ and R$_6$ are each hydrogen;

G$_5$, the radicals R$_1$, R$_2$, R$_3$, R$_4$ and R$_5$ independently of one another are each Q$_3$ and R$_6$ is hydrogen;

G$_6$, the radicals R$_1$, R$_2$, R$_3$, R$_4$, R$_5$ and R$_6$ Independently of one another are each Q$_3$; and Q$_1$ is —T$_1$, —COT$_1$, —COH, —COOT, or —CONT$_1$T$_2$; and Q$_2$ is —T$_3$, —COT$_1$, —COH, —COOT$_1$ or CONT$_1$T$_2$; and Q$_3$ is —T$_4$.

T$_3$ is preferably C$_1$–C$_{18}$alkyl, C$_3$–C$_{12}$alkenyl, C$_3$alkynyl; or C$_1$C$_{18}$alkyl, cyclohexyl, C$_7$–C$_{18}$phenylalkyl, C$_7$–C$_{18}$alkylphenyl, phenyl in each case substituted by one or more —SO$_3$H, —SO$_3$M, —COOR, COOM, —CONRR', OCOR, —OCONRR', —NRCOR', —NRCOOR, or —NRCONR'R";

T$_4$ is preferably C$_1$–C$_{18}$alkyl, cyclohexyl, C$_7$–C$_{18}$phenylalkyl, C$_7$–C$_{18}$alkylphenyl, C$_6$–C$_{18}$phenyl in each case substituted by one or more —COOM.

Further preferred substituents of the novel compounds of the formula III are as indicated earlier on above for compounds G$_1$–G$_6$ of the formula I.

The invention further provides compositions comprising

A) an organic material sensitive to exposure to light, oxygen and/or heat, and

B) as stabilizer, a mixture of compounds of the formula I, and also provides a method of stabilizing organic material with respect to exposure to light, oxygen and/or heat, which comprises adding or applying to said material the mixture of compounds of the invention, and also provides for the use of a mixture of compounds of formula I as stabilizers with respect to exposure to light, oxygen and/or heat.

The mixture of the invention may be used to protect a diversity of organic material sensitive to damage by light, heat, oxygen, etc.; examples include oils, fats, waxes, automobile finishes, woodcoatings, paints such as emulsion paints or paints for mineral construction materials such as concrete or asphalt, for example, reprographic material such as photographs, films, printing inks, and corresponding recording materials, wood or material comprising wood, paper, leather, plastics and coatings thereon, textiles, cosmetics, sun protection compositions, greenhouse films, windows, window coatings or window films (solar films). Possibilities include both the protection of the material itself, into which the stabilizer mixture of the invention is incorporated, and the protection of a material to which the stabilizer mixture of the invention is applied either directly or in the form of a protective layer. Examples of such protective layers include coatings, top layers of laminates, impregnated articles, and also covers, screens or packaging of all kinds. Possibilities thus also include, for example, the protection of seed, skin tissue, hair or hair colorations, or of active substances such as pesticides, herbicides or fungicides.

Of particular interest is the use in polymeric materials, as are present in plastics, rubbers, paints, varnishes or adhesives. Where the material to be stabilized comprises photographic material, its structure is preferably as described in U.S. Pat. No. 5,538,840 from column 25 line 60 to column 106 line 35, and the mixture of the invention of formula I is employed in analogy to the employment of the compound of the formula (I) described in U.S. Pat. No. 5,538,840, and/or polymers prepared from it; the sections of U.S. Pat. No. 5,538,840 referred to are considered part of the present description.

Stabilizers of the invention comprising compounds of the formula I of the carboxylate and/or sulfonate type are particularly suitable for stabilizing coating compositions or emulsion paints that are based on water, and also inks for ink-jet printing.

Preferred materials which may be stabilized in accordance with the invention are synthetic organic polymers, prepolymers and photographic material. The term prepolymers is intended to denote those monomeric or oligomeric compounds which may be converted into the high molecular mass form (polymer) under the influence of heat or radiation, for example UV radiation, electron beams or X-rays, and/or under the influence of chemical components such as crosslinkers, couplers or catalysts.

The stabilizer of the invention is notable in particular for an outstanding protective action and also a high level of compatibility with the organic material to be stabilized, and good processing properties. Very particularly, it is suitable as a light stabilizer (UV absorber).

Examples of polymers which may be stabilized in this way are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or α-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) Including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephithalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyimides, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins:

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The amount of stabilizer to be used is guided by the organic material to be stabilized and by the intended use of the stabilized material. In general, the composition of the invention contains from 0.01 to 15, in particular from 0.05 to 10, and especially from 0.1 to 5 parts by weight of the stabilizer (component B) per 100 parts by weight of component A.

Besides the stabilizer of the formula I, the compositions of the invention may comprise other stabilizers or other additions, such as antioxidants, further light stabilizers, metal deactivators, phosphites or phosphonites, for example. Examples of these are the following stabilizers:

1. Antioxidants 1.1. Alkylated monophenols, for example 2,6-di-tert-butyl-4-methylphenol, 2-tert-butyl-4,6di-methylphenol, 2,6-di-tert-butyl-4-ethylphenol, 2,6-di-tert-butyl-4-n-butylphenol, 2,6di-tert-butyl-4-isobutylphenol, 2,6-dicyclopentyl-4-methylphenol, 2-(α-methylcyclohexyl)-4,6-dimethyl-phenol, 2,6dioctadecyl-4-methylphenol, 2,4,6tricyclohexylphenol, 2,6-di-tert-butyl-4-meth-oxymethylphenol, nonylphenols which are linear or branched in the side chains, e.g. 2,6-di-nonyl-4-methylphenol, 2,4dimethyl-6-(1'-methylundec-1'-yl)phenol, 2,4-dimethyl-6-(1'-methyl-heptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4dioctyl thiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1,5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6tert-butyl-2-methylphenol), 4.4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis[6-(α-methylbenzyl)-4-nonylphenol], 2.2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5-methylbenzyl)-6-tert-butyl-1-4-methylphenyl]terophthalate, 1,1-bis-(3,5-dimethyl-2-hydroxyphenyl)butane, 2,2-bis(3,5-di-tert-butyl-4hydroxyphenyl)propane, 2,2-bis-(5-tert-butyl-4-hydroxy2-methylphenyl)$_4$-n-dodecylmercaptobutane, 1,1,5,5-tetra(S-tert-butyl-4-hydroxy-2-methylphenyl)pentane.

1.7. O—, N—and S-benzyl compounds, for example 3,5,3',5'-tetra-tert-butyl-4,4'-dihydroxydibenzyl ether, octadecyl-hydroxy-3,5-dimethylbenzylmercaptoacetate, tridecyl-4-hydroxy-3,5di-tert-butylbenzylmercaptoacetate, tris(3,5di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5di-tert-butyl-2-hydroxybenzyl) malonate, di-octadecyl-2-(3-tert-butyl-4-hydroxy-5-methylbenzyl)malonate, di-dodecylmercaptoethyl-2,2-bis (3,5-di-tert-butyl-4-hydroxybenzyl)malonate, bis[4-(1,1,3, 3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis (octylmercapto)-6-(3,5-di-ter-butyl-4-hydroxyanilino)-1,3, 5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris-(3,5-di-tert-butyl-4-hydroxyphenylethyl)-1,3,5-triazine, 1,3,5tris(3,5di-tert-butyl-4-hydroxy-phenylpropionyl)-hexahydro-1,3,5-triazine, 1,3,5-tris(3,5-dicyclohexyl-4-hydroxybenzyl)iso cyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of B-(3.5di-tert-butyl-4-hydroxyphenyl) propionic acid with mono- or polyhydric alcohols, e.g. with methanol, ethanol, n-octanol, i-octanol, octadecanol, 1,6hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N-bis(hydroxyethyl) oxamide, 3-thiaundecanol, 3-thiapentadecanol, trimethylhexanediol, trimethylol-propane, 4-hydroxymethyl-1-phospha-2,6,7-trioxabicyclo[2.2.2] octane.

1.14. Esters of β-(5-tert-butyl-4-hydroxy-3-methylphenyl)propionic acid with mono- or -poly-hydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl) oxamide, 3-thiaundecanol, 3thiapentadecanol, trimethylhexanediol, trimethyl-olpropane, 4-hydroxymethyl-1-phospha-2,6,7-trioxabicyclo[2.2.2] octane; 3,9-bis[2-[3-(3-tertbutyl-4-hydroxy-5methylphenyl) propionyloxy]-1,1-dimethylethyl]-2,4,8, 10-tetraoxaspiro [5.5]-undecane.

1.15. Esters of β-(3.5-dicyclohexyl-4-hydroxyphenyl) propionic acid with mono- or polyhydric alcohols, e.g. with methanol, ethanol, octanol, octadecanol, 1,6-hexanediol, 1,9nonanediol, ethylene glycol, 1,2propanediol, neopentyl glycol, thiodiethylene glycol, diethylene glycol, tri-ethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3.5di-tert-butyl-4-hydroxyphenyl acetic acid with mono- or polyhydric alcohols, e.g. with methanol, ethanol, octanol, octadecanol, 1,6-hexanediol, 1,9nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3.5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard™XL-1, supplied by Uniroyal).

1.18. Ascorbic acid (vitamin C)

1.19. Aminic antioxidants, for example N,N'-di-isopropyl-p-phenylenediamine, N,N-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoyl-aminophenol. 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-3'-tert-butyl-2'-hydroxy-5'-methylphenyl)-5chlorobenzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5chlorobenzotriazole, 2-(3'-tert-butyl-2'-hydroxy-5-(2-methoxy)carbonylethyl)phenyl)benzotriazole, 2-(3'-tertbutyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxy-phenyl)benzotriazole, 2-(3-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-ylphenyl, 2-[2'-hydroxy-3'(α,α-dimethylbenzyl)-5'-(1,1,3,3-tetramethylbutyl)phenyl]-benzotriazole; 2-[2'-hydroxy-3'-(1, 1,3,3-tetramethylbutyl)-5'.(α,α-dimethylbenzyl)phenyl]benzotriazole.

2.2. 2-Hydroxybenzophenones, for example the 4-hydroxy, 4-methoxy, 4-octyloxy, 4-decyloxy, 4-dodecyloxy, 4benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano->methyl-β-methoxycinnamate, butyl α-cyano-βmethyl-p-methoxycinnamate, methyl α-carbomethoxy-p-methoxycinnamate and N-(β-carbomethoxy-βcyanovinyl)-2-methylindoline.

2.5. Nickel compounds, for example nickel complexes of 2,2'-thiobis[4<1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2.2,6,6-tetramethyl-4-piperidyl) pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6 -dichloro-1,3,5-triazine, a condensate of 1,2-bis(3-aminopropylamino)ethane and 2,4,6 trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [19226864-71]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro-[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly(methylpropyl-3-oxy-4-(2,2,6,6-tetramethyl-4piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2-dioctyloxy-5,5-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1.3.5-triazines, for example 2,4,6-tris(2-hydroxy-4-octyloxyphenyl)-1,3,5-triazine, 2-(2-hydroxy-4-octyloxyphenyl)-4,6bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)1,3,5-triazine, 2-(2-hydroxy-4-octyloxyphenyl)-4,6-bis(4-methylphenyl)-1,3,5-triazine, 2-(2-hydroxy-4-dodecyloxyphenyl)4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3butyloxypropoxy) phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 214-(dodecyloxy/tridecyloxy-2-hydroxypropoxy)-2-hydroxyphenyl]-4,6-bis(2,4-dimethylphenyl)1,3,5triazine, 2-[2-hydroxy-4-(2-hydroxy-3dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]1,3,5-triazine, 2-(2-hydroxyphenyl)-4-(4-methoxyphenyl)-6-phenyl-1,3,5- triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-4-butyl-4hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4di-tert-butylphenyl) pentaerythritol diphosphite, bis(2,4-di-cumylphenyl) pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 6-fluoro-2,4,8,10tetra-tert-butyl-12-methyl-dibenz[d,g]-1, 3,2-dioxaphosphocin, 2,2',2"-nitrilo-[triethyltris(3,3',5,5'-tetra-tert-butyl-1,1'-biphenyl-2,2-dyl)phosphite], 2-ethylhexyl(3,3',5,5'-tetra-tert-butyl-1,1'-biphenyl-2,2-yl)phosphite, 5-butyl-5-ethyl-2-(2,4,6-tri-tert-butylphenoxy) - 1,3,2-dioxaphosphirane.

The following phosphites are especially preferred:

Tris(2,4-di-tert-butylphenyl) phosphite (Irgafos®168, Ciba-Geigy), tris(nonylphenyl) phosphite,

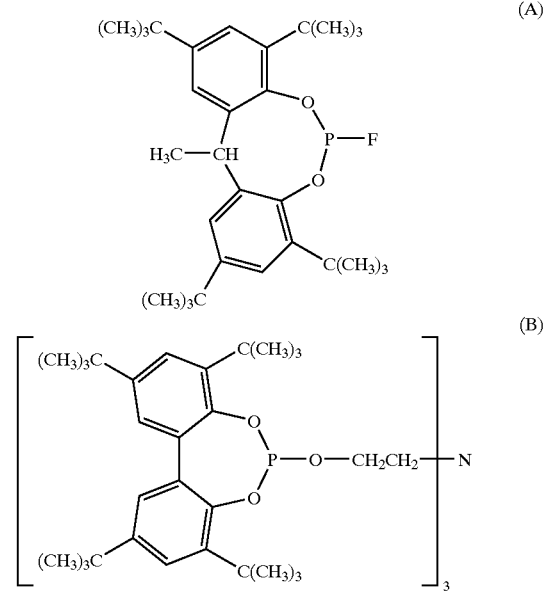

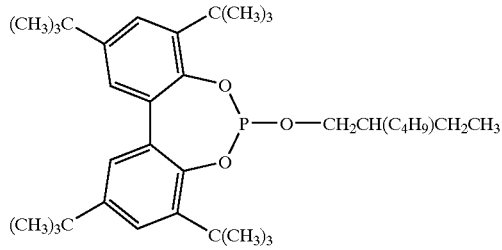

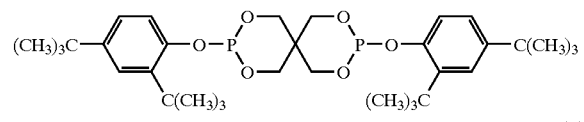

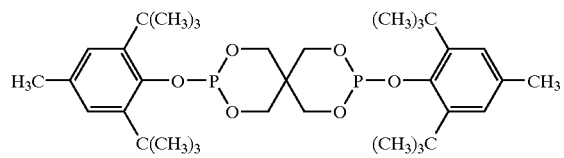

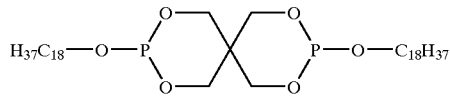

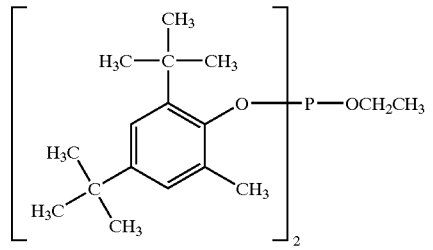

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N -hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-hepta-decylnitrone, N-octadecyl-alpha-hexadecylnitrone, nitrone derived from N,N-dialkylhydroxyl-amine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercapto benzimidazole, zinc dibutyldithiocarbamate, dioctadecyl disulfide, pentaerythritol tetrakis(βdodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene) sorbitol, 1,3:2,4-di(paramethyldibenzylidene) sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A4316611; DE-A4316622; DE-A-4316876; EP-A-0589839 or EP-A-0591102 or 3-[4-(2-acetoxyethoxy) phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl-5,7-di-ten-butyl-benzofuran-2-one, 3-(3,5-dimethyl-4-pivaloyloxyphenyl)-5,7-di-tert-butyl benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The nature and amount of the further stabilizers added is determined by the nature of the substrate to be stabilized and by its intended use; in many cases, from 0.1 to 5% by weight, based on the organic material to be stabilized, is used.

With particular advantage, the stabilizer of the invention may be used in compositions comprising as component A a synthetic organic polymer, especially a thermoplastic polymer, or a binder for coating materials such as paints, for example, or a reprographic material, especially photographic material.

The reprographic material, especially colour photographic material, to be stabilized with advantage in accordance with the present invention is, for example, material as described in Research Disclosure 1990, 31429 (pages 474–480), in USA-5538840 columns 26 to 106, in GB-A-2319523, or in DE-A-19750906, page 22, line 15, to page 105, line 32. Preference is given to use in a layer comprising silver halide or in the protective layer of a colour photographic material, especially of a colour film or of a colour photographic paper.

Suitable thermoplastic polymers include, for example, polyolefins (e.g. as per 1.–3. of the above list) and also polymers containing heteroatoms in the main chain, such as thermoplastic polymers containing nitrogen, oxygen and/or sulfur, especially nitrogen or oxygen, in the main chain; examples of such polymers are set out in the above list, inter alia, under 13.–20., with particular importance being possessed by polyamides, polyester and polycarbonate (17.–19.).

Incorporation into the synthetic organic polymers or prepolymers may be effected by adding the stabilizer of the invention and any further additives in accordance with the methods that are customary in the art. Incorporation may take place judiciously before or during shaping, for example by mixing the pulverulent components or by adding the stabilizer to the melt or solution of the polymer, or by applying the dissolved or dispersed compounds to the polymer, with or without subsequent evaporation of the solvent. Elastomers may also be stabilized in the form of latices. A further possibility for incorporating the compounds of the invention into polymers is to add them before or during the polymerization of the corresponding monomers, and/or prior to crosslinking.

The addition of the compounds or mixtures of the invention to the plastics to be stabilized may also take place in preformulated form, for example in a form containing 2.5–98% by weight of the stabilizer of the invention in addition to at least one other component, e.g. an emulsifier or dispersant, or in the form of a masterbatch containing these compounds, for example, in a concentration of from 2.5 to 25% by weight.

The incorporation may judiciously be effected in accordance with the following methods:

as an emulsion or dispersion (e.g. to latices or emulsion polymers)

as a dry mixture during the mixing of additional components or polymer mixtures by direct addition to the processing apparatus (e.g. extruder, internal mixer, etc.)

as a solution or melt.

The stabilized polymer compositions obtained in this way may be converted by the customary methods, such as by hotpressing, spinning, extrusion or injection moulding, for example, into shaped articles, such as fibres, films, strips, sheets, sandwich plates, vessels, pipes and other profiles, for example.

The invention therefore further provides the use of the polymer composition of the invention for producing a shaped article.

Use in multilayer systems is also of interest. In this case, a polymer composition of the invention comprising a relatively large amount of stabilizer of formula I, for example 1–15% by weight, is applied in a thin film (10–100 μm) to a shaped article made from a polymer containing little or no stabilizer of the invention. The application may be synchronous with the shaping of the base article, for example by coextrusion. Alternatively, application may take place to the base article in its already shaped form, for example by lamination with a film or by coating with a solution. The outer layer or outer layers of the finished article have the function of a UV filter which protects the interior of the article against UV light. The outer layer preferably contains 1–15% by weight, in particular 5–10% by weight, of at least one stabilizer of formula I.

The present invention therefore further provides for the use of the polymer composition of the invention for producing multilayer systems where the outer layer(s) in a thickness of 10–100 μm comprises (comprise) a polymer composition of the invention while the inner layer contains little or no stabilizer of formula I.

The polymers thus stabilized are notable for high weathering stability, and in particular by high resistance to UV light. As a result, they retain their mechanical properties and also their colour and gloss for a long time, even when used outdoors.

Particular interest attaches to the use of the mixtures of the formula I of the invention as stabilizers for coatings, for example for surface coatings. The invention therefore also provides those compositions whose component A is a film forming binder.

The coating composition of the invention preferably contains 0.01–10 parts by weight, in particular 0.05–10 parts by weight, especially 0.1–5 parts by weight, of the stabilizer B of the invention per 100 parts by weight of solid binder A.

Here again, multilayer systems are possible, in which case the concentration of component B in the top layer may be relatively high: for example, from 1 to 15 parts by weight, especially 310 parts by weight, of B per 100 parts by weight of solid binder A.

The use of the stabilizer of the invention in coatings provides the additional advantage that delamination, i.e. the flaking of the coating from the substrate, is prevented. This advantage is manifested in particular in the case of metallic substrates, including multilayer systems on metallic substrates.

Suitable binders (component A) are in principle all of those common in the art, examples being those as described in Ullmann's Encyclopedia of Industrial Chemistry, 5th ed., Vol. A18, pp. 368–426, VCH, Weinheim 1991. In general, the binder in question is a film-forming binder based on a thermoplastic or thermosetting resin, predominantly on a thermosetting resin. Examples of such are alkyd, acrylic, polyester, phenolic, melamine, epoxy and polyurethane resins and mixtures thereof.

Component A may be a cold curable or a heat curable binder, the addition of a curing catalyst may be advantageous. Suitable catalysts which accelerate the curing of the binder are described, for example, in Ullmann's Encyclopedia of Industrial Chemistry, Vol. A18, p.469, VCH Verlagsgesellschaft, Weinheim 1991.

Preference is given to coating compositions wherein component A is a binder comprising a functional acrylic resin and a crosslinker.

Examples of coating compositions with specific binders are:
1. Coating materials based on cold or hot crosslinkable alkyd, acrylic, polyester, epoxy or melamine resins or mixtures of such resins, with or without the addition of a curing catalyst;
2. Two component polyurethane coating materials based on hydroxyl-containing acrylic, polyester or polyether resins and on aliphatic or aromatic isocyanates, isocyanurates or polyisocyanates;
3. One component polyurethane coating materials based on block isocyanates, isocyanurates or polyisocyanates which are deblocked during baking; if desired, the addition of melamine resins is also possible;
4. One component polyurethane coating materials based on aliphatic or aromatic urethanes or polyurethanes and on hydroxyl-containing acrylic, polyester or polyether resins;
5. One component polyurethane coating materials based on aliphatic or aromatic urethane acrylates or polyurethane acrylates having free amine groups in the urethane structure and on melamine resins or polyether resins, with or without addition of a curing catalyst;
6. Two component coating materials based on (poly) ketimines and on aliphatic or aromatic isocyanates, isocyanurates or polyisocyanates;
7. Two component coating materials based on (poly) ketimines and on an unsaturated acrylic resin or a polyacetoacetate resin or a methacrylamidoglycolate methyl ester;
8. Two component coating materials based on carboxyl- or amino-containing polyacrylates and polyepoxides;
9. Two component coating materials based on acrylic resins containing anhydride groups and on a polyhydroxy or polyamino component;
10. Two component coating materials based on anhydrides containing acrylate and on polyepoxides;
11. Two component coating materials based on (poly) oxazolines and acrylic resins containing anhydride groups, or unsaturated acrylic resins, or aliphatic or aromatic isocyanates, isocyanurates or polyisocyanates;
12. Two component coating materials based on unsaturated polyacrylates and polymalonates,
13. Thermoplastic polyacrylate coating materials based on thermoplastic acrylic resins or externally crosslinking acrylic resins in combination with etherified melamine resins;
14. Coating systems based on siloxane modified or fluorine modified acrylic resins.

In addition to components A and B, the coating composition of the invention preferably comprises as component C a light stabilizer of the sterically hindered amine, 2-(2-hydroxyphenyl)-1,3,5-triazine and/or 2-hydroxyphenyl-2H benzotriazole type, as set out for example in the above list under sections 2.1, 2.6 and 2.8. In this context, there is particular technical interest in the addition of 2-monoresorcinyl-4,6-diaryl-1,3,5-triazines and/or 2-hydroxyphenyl-2H -benzotriazoles.

In order to achieve maximum light stability, there is particular interest in the addition of sterically hindered amines, as set out in the above list under 2.6. The invention therefore additionally provides a coating composition which besides components A and B comprises as component C a light stabilizer of the sterically hindered amine type.

The stabilizer in question is preferably a 2,2,6,6-tetraalkylpiperidine derivative containing at least one group of the formula

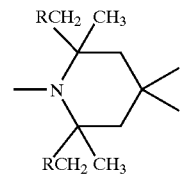

in which R is hydrogen or methyl, especially hydrogen.

Component C is used preferably in an amount of 0.05–5 parts by weight per 100 parts by weight of the solid binder.

Examples of tetraalkylpiperidine derivatives which may be used as component C may be taken from EP-A-356677, pages 3–17, sections a) to f). The stated sections of this EP-A are considered part of the present description. It is particularly judicious to use the following tetraalkylpiperidine derivatives:
Bis(2,2,6,6-tetramethylpiperidin-4-yl) succinate,
Bis(2,2,6,6-tetramethylpiperidin-4-yl) sebacate,
Bis(1,2,2,6-pentamethylpiperidin-4-yl) sebacate,
Di(1,2,2,6,6pentamethylpiperidin-4-yl) butyl(3,5-di-tert-butyl-4-hydroxybenzyl)malonate,
Bis(1-octyloxy-2,2,6,6-tetramethylpiperidin-4-yl) sebacate,
Tetra(2,2,6,6-tetramethylpiperidin-4-yl) butane-1,2,3,4-tetracarboxylate, Tetra(1,2,2,6,6-pentamethylpiperidin-4-yl) butane-1,2,3,4-tetracarboxylate, 2,2,4,4-Tetramethyl-7-oxa-3,20-diaza-21-oxodispiro[5.1.11.2]heneicosane, 8-Acetyl-3-dodecyl-1,3,8-triaza-7,7,9,9-tetramethylspiro[4,5] decane-2,4-dione, 1,1-Bis(1,2,2,6,6-pentamethylpiperidin-4-yl-oxycarbonyl)-2-(4-methoxyphenyl)ethene, or a compound of the formulae

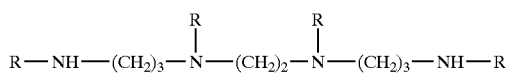

where R =

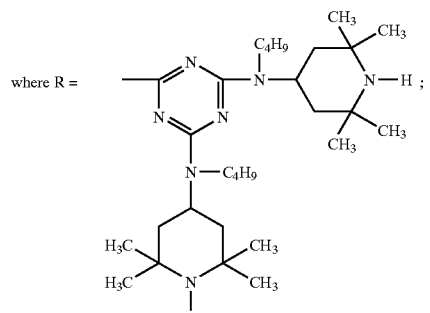

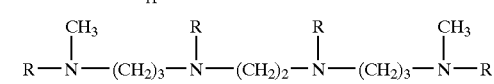

where R =

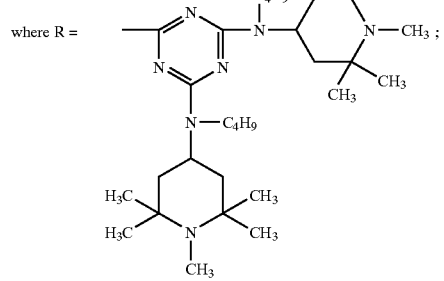

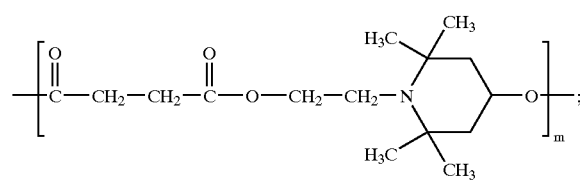

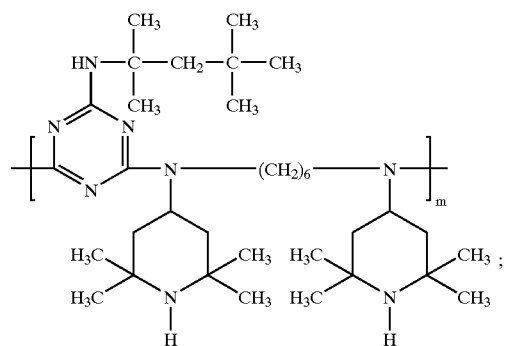

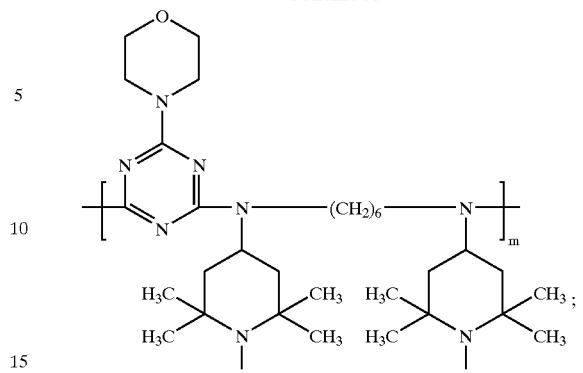

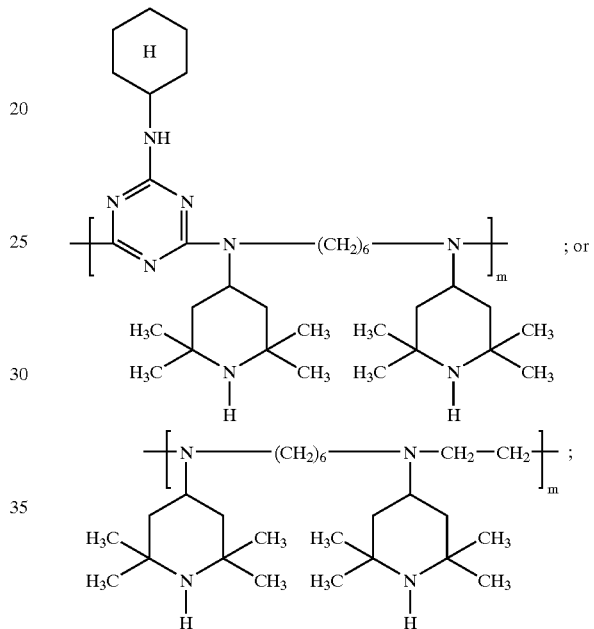

where m is 550.

Besides the components A, B and, if present, C, the coating composition may comprise further components, examples being solvents, pigments, dyes, plasticizers, stabilizers, thixotropic agents, drying catalysts, and/or levelling assistants.

Examples of possible components are those described in Ullmann's Encyclopedia of Industrial Chemistry, 5th Ed, Vol. A18, pp. 429471, VCH, Weinheim 1991.

Possible drying catalysts and curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co, or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate and dibutyltin dioctoate.

Examples of amines are especially tertiary amines, such as tributylamine, triethanolamine, N-methyldiethanolamine, N-dimethylethanolamine, N-ethyl morpholine, N-methylmorpholine or diazabicyclooctane (triethylenediamine), and their salts. Further examples are quaternary ammonium salts, such as trimethylbenzylammonium chloride, for example.

Resins containing amino groups are simultaneously binders and curing catalysts. Examples thereof are amino-containing acrylate copolymers.

As curing catalysts it is also possible to use phosphines, such as triphenylphosphine.

The coating compositions of the invention may also comprise radiation curable coating compositions. In this case, the binder essentially comprises monomeric or oligomeric compounds having ethylenically unsaturated bonds (prepolymers) which following application are cured—that is, converted into a crosslinked, high molecular mass form—by means of actinic radiation. Where the system in question is a UV curing system, it generally further comprises a photoinitiator.

Corresponding systems are described in the abovementioned publication, Ullmann's Encyclopedia of Industrial Chemistry, 5th Ed, Vol. A18, pages 451–453. In radiation curable coating compositions, the stabilizers of the invention may be used even without the addition of sterically hindered amines.

The coating compositions of the invention may be applied to any desired substrates, examples being metal, wood, plastic, or ceramic materials. In the case of automotive coating systems, they are preferably used as basecoat material. Where the topcoat comprises two layers of which the bottom layer is pigmented and the top layer is not pigmented, the coating composition of the invention may be used for the top or the bottom layer or for both layers, but preferably for the bottom (pigmented) layer.

Likewise preferred is the use of the compounds of the invention in wood preservation, for example by incorporation of the stabilizer of the formula I into a varnish, stain or impregnant for wood. The present invention therefore further provides a method of stabilizing a wood surface against damaging weathering effects, especially of light, oxygen and/or heat, which comprises treating the wood with a stabilizer of the formula I, in particular by applying a varnish, stain and/or impregnant comprising a stabilizer of the formula I. With the aid of the method of the invention it is possible to achieve marked reductions in unwanted discolorations such as yellowing or bleaching of the wood. Mixtures of compounds of the formula I are preferably used as part of an impregnant, a stain, or a topcoat.

In the case of application to wood, it is also possible to use a compound of the formula I in which $R_9$ has one of the definitions given for $R_{11}$, an example being the compound 1 (2,4,6 tris(2-hydroxy-4-[1-ethyloxycarbonyl-1-methylethoxy]phenyl)-1,3,5triazine). Preferred compounds in these compositions are as indicated earlier on above.

Often, hindered amines are used at the same time, examples being those as described earlier on above, especially in amounts of 0.1–10%, e.g. 0.2–5%, in particular 0.2–2% based on the overall weight of binder and solvent. Particular preference for wood applications is given to hindered amines of the hydroxylamine type (as described in EP-A-309401, for example) or corresponding N-oxides, and also salts of these compounds.

Where application is made in the form of a stain or impregnant, it is preferred to use the solvent selected, for example, from aliphatic, cycloaliphatic and/or aromatic hydrocarbons, alcohols, ethers, esters, ketones, glycols, glycol ethers, glycol esters, polyglycols or mixtures thereof. In this case the binder is preferably an alkyd resin, modified alkyd resin, self-crosslinking or non self-crosslinking acrylic resin, a polyester resin, an oxidatively drying oil, a phenolic resin, nitrocellulose, or a corresponding mixture.

Customary additives such as fungicides or insecticides are possible, e.g. tributylin oxide, phenylmercury salts, copper naphthenate, 1-chloronaphthalene, pentachlorophenol, dieldrin, lindane, azaconazole, cypermethrin, benzalkonium hydrochloride, propiconazole or parathion.

Topcoats on wood normally comprise a binder, dissolved or dispersed in an organic solvent or water or mixture of an organic solvent and water. The binder is typically a resin which is airdrying or cures at room temperature (i.e. in the range approximately 10–30° C.). Examples of such binders are nitrocellulose, polyvinyl acetate, polyvinyl chloride, unsaturated polyester resins, polyacrylates, polyurethanes, epoxy resins, phenolic resins, and especially alkyd resins. Also possible are corresponding mixtures and also radiation-curable and/or solvent free systems; illustrative examples are mixtures of acrylates or methacrylates, unsaturated polyester/styrene mixtures, or mixtures of other ethylenically unsaturated monomers or oligomers.

Examples of wood surfaces treated in accordance with the invention are those of furniture, woodblock flooring, panels and wood veneers, along with exterior applications such as fences, constructional elements, wood facings, window frames or door frames, etc.

The coating compositions of the invention may be applied to the substrates by the customary methods, for example by brushing, spraying, flowcoating, dipping or electrophoresis; see also Ullmann's Encyclopedia of Industrial Chemistry, 5th Ed., Vol. A118, pp. 491–500.

Depending on the binder system, the coatings may be cured at room temperature or by heating. Preferably, the coatings are cured at 50150° C., powder coatings or coil coatings also at higher temperatures.

The coatings obtained in accordance with the invention have an outstanding resistance to harmful influences of light, oxygen and heat; reference should be made in particular to the good light stability and weathering stability of the coatings thus obtained, for example surface coatings.

The invention therefore also provides a coating, especially a surface coating, which is stabilized against harmful influences of light, oxygen and heat as a result of the addition of a compound of the formula I. The surface coating is preferably a basecoat for automobiles or a wood coating. The invention further embraces a method of stabilizing a coating based on organic polymers against damage by light, oxygen and/or heat, which comprises admixing with the coating composition a compound of the formula I, and also provides for the use of compounds of the formula I in coating compositions as stabilizers against damage by light, oxygen and/or heat.

The coating compositions may comprise an organic solvent or solvent mixture in which the binder is soluble. Alternatively, the coating composition may be an aqueous solution or dispersion. The vehicle may also be a mixture of an organic solvent and water. The coating composition may also be a high solids coating material or may be solvent-free (e.g. powder coating). Powder coatings are those, for example, as described in Ullmann's Encyclopedia of Industrial Chemistry, 5th Ed., A18, pages 438–444. The powder coating may also be present in the form of a powder slurry, i.e. a dispersion of the powder, preferably in water.

The pigments may be organic, inorganic or metallic pigments. Preferably, the coating compositions of the invention contain no pigments and are used as clearcoat.

Preference is likewise given to the use of the coating composition as a basecoat for applications in the automotive industry, especially as the pigmented topcoat of the coating. The use for coats lying above this, however, is also possible.

The following examples provide a further description of the invention without representing any restriction. Parts and percentages therein are by weight; it an example mentions room temperature, it means a temperature in the range 20–25° C. In the case of solvent mixtures, such as for chromatography, parts by volume are stated. These provisions apply unless different details are given.

| Abbreviations: | |
|---|---|
| THF | tetrahydrofuran |
| abs. | anhydrous |
| m.p. | melting point or melting range |
| NMR | nucleomagnetic resonance |
| torr | = mmHg (1 torr corresponds to about 133 Pa) |
| $T_g$ | glass transition temperature |
| h | hours |

EXAMPLE 1

UV-Absorber Mixture Comprising 2-(2, 4dihydroxyphenyl)-4,6-bis(2-hydroxy-4(1-methoxycarbonylpentoxy)phenyl)-1,3,5-triazine, 2, 4,6-tris(2-hydroxy-4-(1-methoxycarbonyl-pentoxy) phenyl)-1,3,5triazine and 2-(2,4-di (methoxycarbonylpentoxy)phenyl)-4.6-bis(2-hydroxy 4(1-methoxycarbonylpentoxy)phenyl)1,3, 54triazine 12.15 g of tris(2.4-dihydroxyphenyl)-1,3,5-triazine, 10.5 g of sodium carbonate, 20 ml of dimethylformamide and 20.15 g (96.4 mmol) of methyl bromocaproate are heated at 90° C. for 5 h with stirring. The reaction mixture is subsequently admixed with water and subjected to extraction with heptane and the extracts are concentrated to give 23.78 g of a bright orange coloured resin comprising the following components:

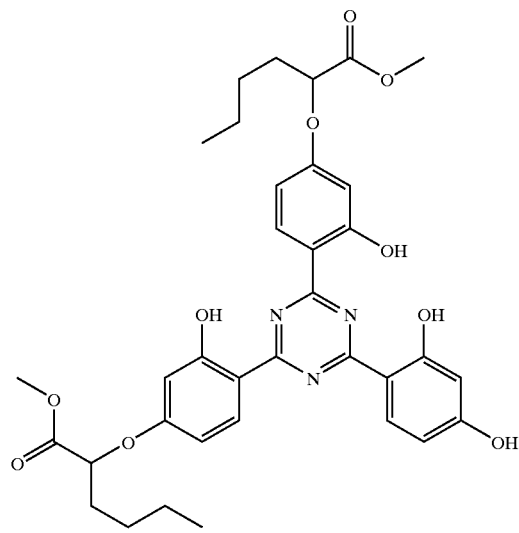

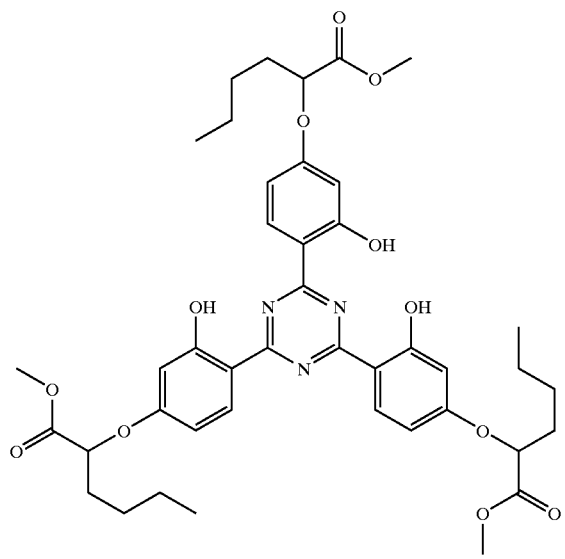

Similar results are obtained if extraction is carried out using, instead of heptane, one of the solvents benzene, toluene, xylene, butyl acetate, ethyl acetate, ethyl methyl ketone, methyl isobutyl ketone or mixtures thereof or mixtures with heptane.

EXAMPLE 2

Working as in Example 1 but starting from tris(2,4-dihydroxyphenyl)-1,3,5-triazine and ethyl bromoacetate gives a mixture comprising:

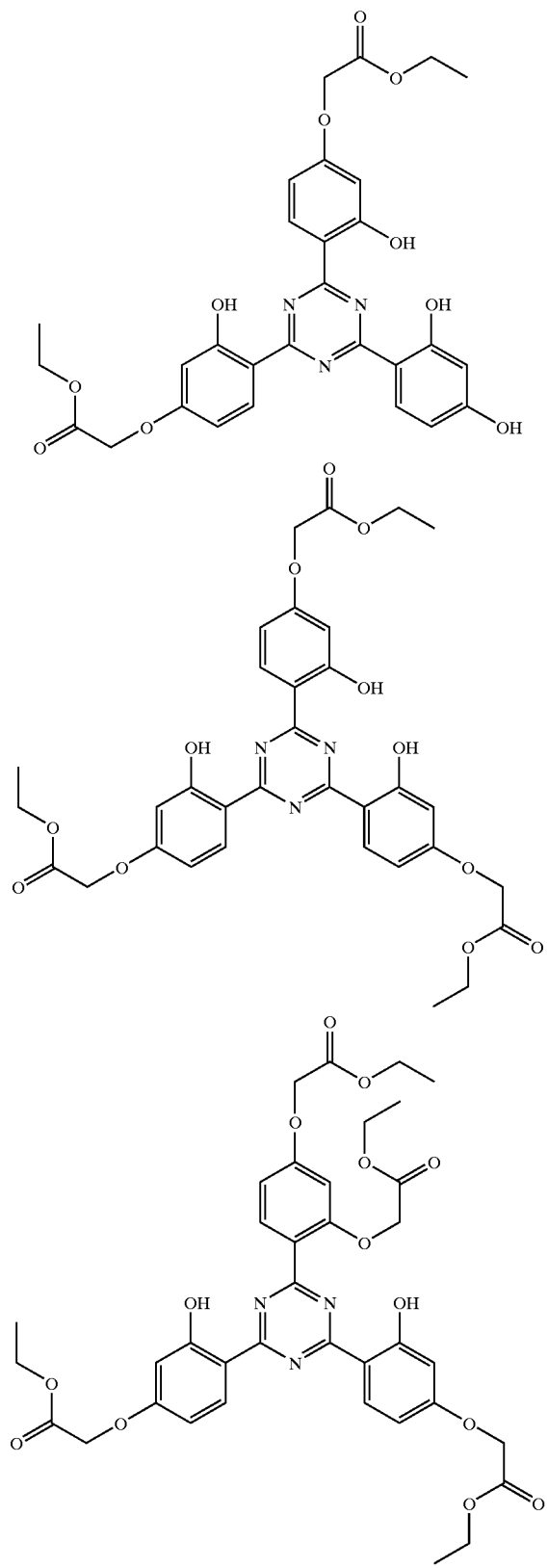
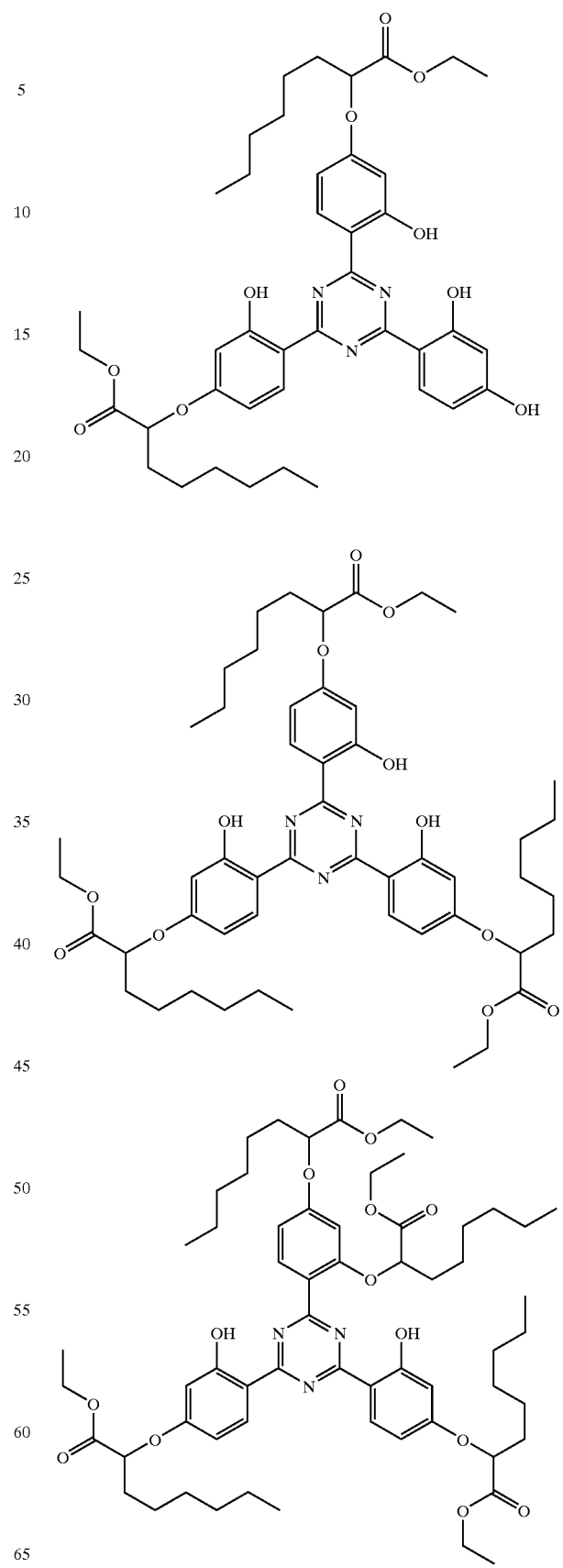
EXAMPLE 3
Working as in Example 1 but starting from tris(2,4-dihydroxyphenyl)-1,3,5triazine and ethyl 2-bromooctanoate gives a mixture comprising:

EXAMPLE 4

Working as in Example 1 but starting from tris(2,4-dihydroxyphenyl)-1,3,5-triazine and methyl 2-bromopropionate gives a mixture comprising:

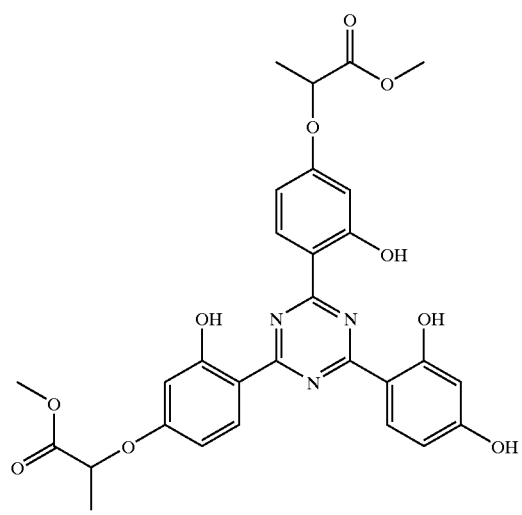

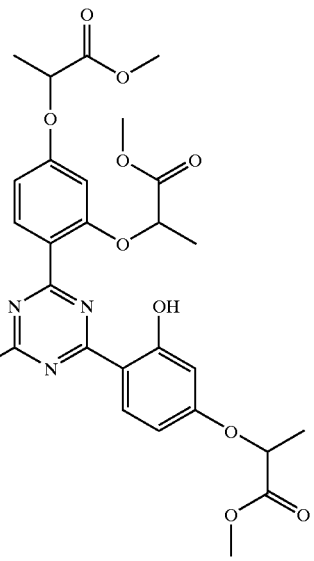

EXAMPLE 4a

Working as in Example 1 but starting from tris(2,4-dihydroxyphenyl-1,3,5-triazine and the equivalent amount of the ester of an octanol isomer mixture of straight-chain and branched-chain $C_7$, $C_8$ and $C_9$ alcohols and bromopropionic acid gives the mixture comprising the components of the following formulae:

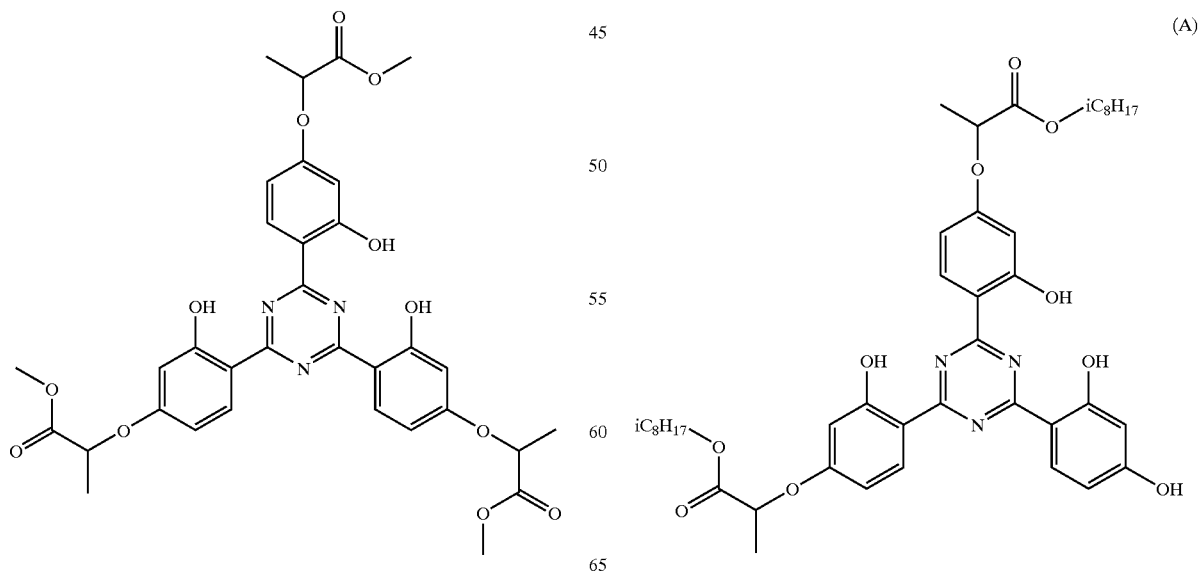

-continued (B)

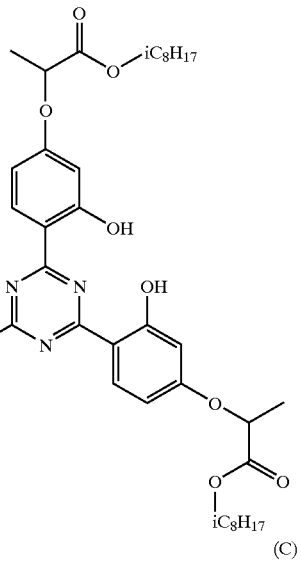

(C)

iC$_8$H$_{17}$: C$_7$–C$_9$alkyl isomer mixture, Yield: 95%.

EXAMPLE 4b 10 g of tris(2,4-dihydroxyphenyl)-1,3,5-triazine, 8.89 g of Na carbonate, 20 ml of dimethylformamide and 17.97 g of α-chloropropionic esters (isomer mixture of C$_7$–C$_9$alcohols in analogy to Example 4a) and 40 ml of toluene are heated at 90° C. for 18 h with stirring. After cooling, water is added and the mixture is subjected to extraction with ethyl acetate. The organic phase is washed a number of times with water and dried. Removal of the solvent gives the product mixture in 77% yield with the principal components stated in Example 4a, containing 31% of the bisalkylated (A), 16% of the trisalkylated (B) and 2% of the tetraalkylated product (C) (HPLC, $^1$H-NMR) as well as monoalkylated product and starting material.

EXAMPLE 4c 10 g of tris(2,4-dihydroxyphenyl)-1,3,5triazine, 8.89 g of Na carbonate, 20 ml of dimethylformamide and 17.97 g of α-chloropropionic esters as in Example 4b are heated at 100° C. for 20 h. After cooling, water is added and the mixture is subjected to extraction with ethyl acetate. The organic phase is washed a number of times with water and dried. Removal of the solvent gives the product mixture as in Example 4a as an orange-coloured resin in 96% yield containing 10% (A), 36% (B) and 42% (C) (HPLC, $^1$H-NMR) as well as monoalkylated products and starting material.

EXAMPLE 4d 10 g of tris(2,4-dihydroxyphenyl)-1,3,5-triazine containing 3 equivalents of dimethylacetamide, 5.40 g of Na carbonate, 13 ml of dimethylformamide and 13.26 g of α-bromopropionic esters (isomer mixture of C$_7$–C$_9$alcohols as in Example 4a) and 13 ml of heptane are heated at 90° C. for 7 h with stirring. After cooling, water is added and the mixture is subjected to extraction with heptane and ethyl acetate. The organic phase is washed a number of times with salt water and water and then dried. Removal of the solvent gives the product mixture as in Example 4a, quantitatively, as an orange-coloured resin containing 30% (A), 41% (B) and 15% (C) (HPLC, $^1$H-NMR) as well as monoalkylated product and starting material.

EXAMPLE 4e 10 g of tris(2,4-dihydroxyphenyl)-1,3,5-triazine containing 3 equivalents of dimethylacetamide, 5.40 g of Na carbonate, 13 ml of dimethylformamide and 13.26 g of α-bromopropionic esters (isomer mixture of C$_7$–C$_9$alcohols as in Example 4a) and 13 ml of toluene are heated at 90° C. for 7 h with stirring. After cooling, water is added and the mixture is subjected to extraction with toluene. The organic phase is washed a number of times with water and then dried. Removal of the solvent gives the product mixture as in Example 4a as an orange-coloured resin containing 12% (A), 58% (B) and 28% (C) (HPLC, $^1$H-NMR) as well as monoalkylated product and starting material; yield 98%.

EXAMPLE 4f 300 g of tris-(2,4-dihydroxyphenyl)-1,3,5-triazine and 258.85 g sodium carbonate are mixed together with 776 ml dimethylformamide and then stirred and heated for 2.5 hours to 130° C. Then the reaction mixture is cooled to 80° C. and a mixture of 539.1 g α-chloropropionic acid octylester isomer mixture (prepared from 2-chloropropionicacid and a mixture of branched and straight C$_7$, C$_8$ and C$_9$ alcohols) in 776 ml Ethylmethylketone is added drop wise in 20 minutes.

The reaction mixture is stirred overnight at 80° C. Then it is cooled to room temperature and filtered. To the filtrate are added 200 ml of toluene and 2000 ml of water. The phases are separated and the organic phase is washed two times with 1000 ml of water. Then the organic phase is dried over MgSO$_4$, filtered, and the solvents evaporated, giving an orange resin with 80% yield containing 22.1% bis-alkylated product A, 34.1% tris-alkylated product B and 11.9% tetra-alkylated product C determined by HPLC and $^1$H-NMR besides mono-alkylated product and starting material.

A
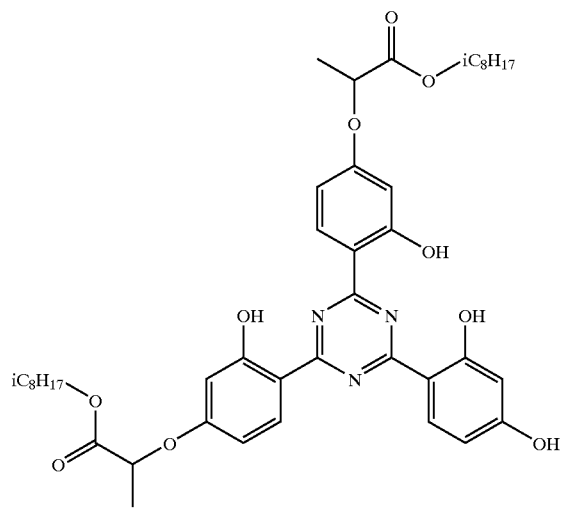

B
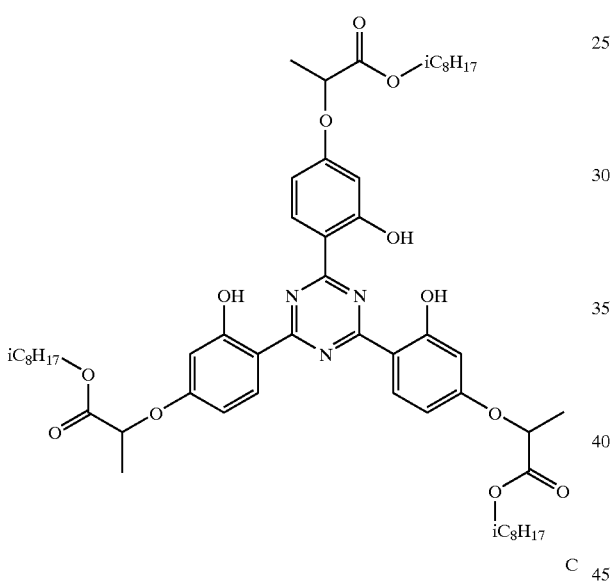

C
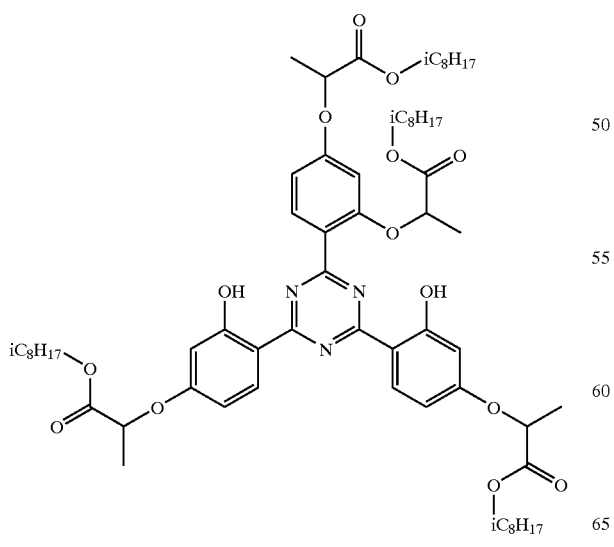

iC$_6$H$_{17}$: branched and straight heptyl, octyl and nonyl alkyl isomer mixture

EXAMPLE 5

UV-Absorber Mixture Comprising 2-(2,4-dihydroxyphenyl)-4,6-bis-(2-hydroxy-4-(1-hydroxycarbonylpentoxy)phenyl)-113,5-triazine, 2,4,6-tris(2-hydroxy-4-(1-hydroxycarbonyl-pentoxy)phenyl)-1,3,5-triazine and 2-(2,4-di(hydroxycarbonylpentoxy)phenyl)-4,6-bis(2-hydroxy-4-(1-hydroxycarbonylpentoxy)phenyl)-1,3,5-triazine 11.5 g of the mixture of compounds from Example 1 are dissolved in 10 ml of DMF at 100° C.

Then a solution of 4.08 g of NaOH in 30 ml of water is added and the reaction mixture is stirred overnight at 100° C. The reaction mixture is neutralized and filtered. The residue is washed with water and dried. This gives 12.32 g of a yellow powder mixture comprising the following components:

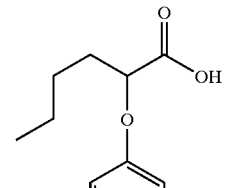
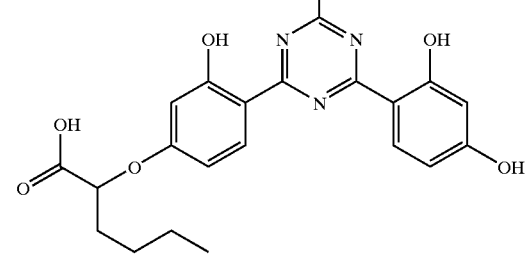
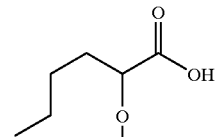
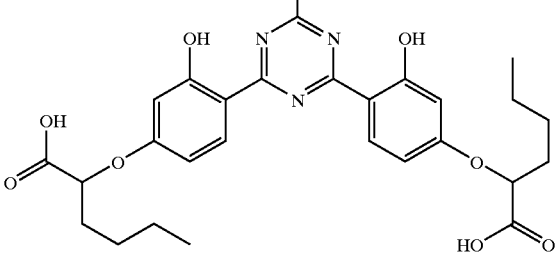

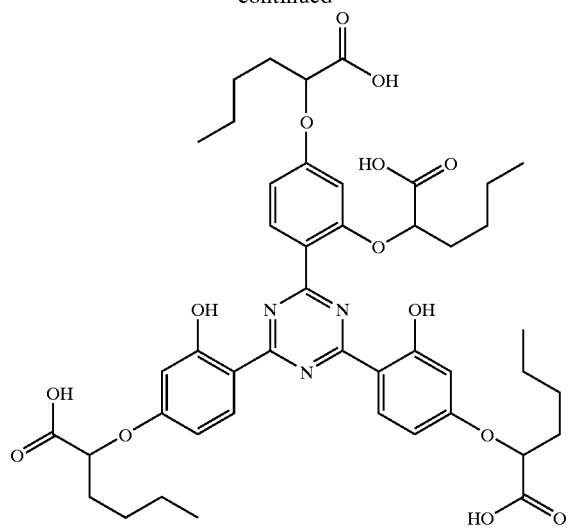
EXAMPLE 6
Working as in Example 5 but starting from the product from Example 2 gives a mixture comprising:
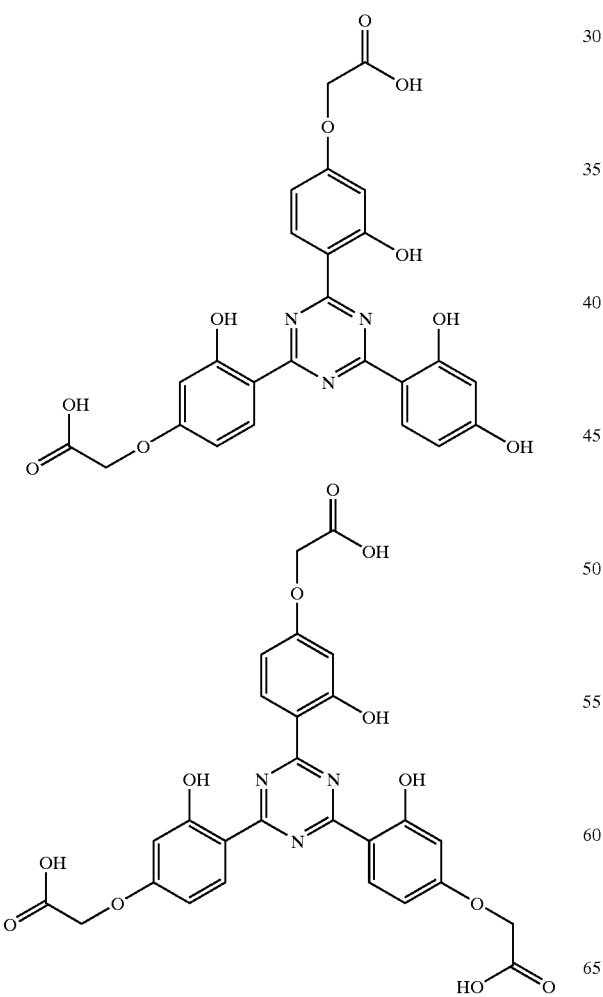
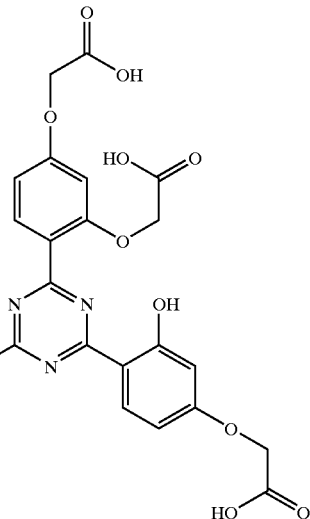
EXAMPLE 7
Working as in Example 5 but starting from the product from Example 3 gives a mixture comprising:
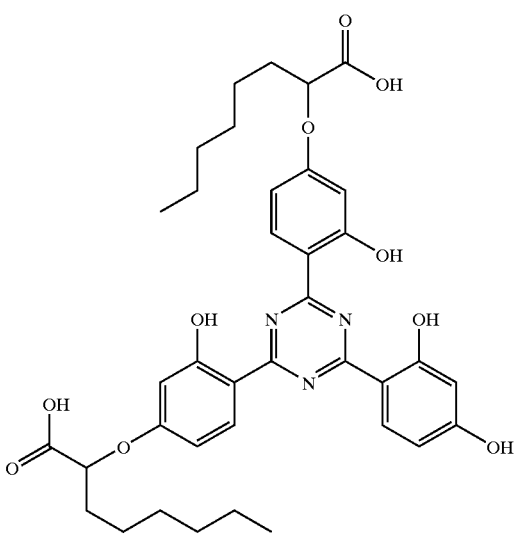

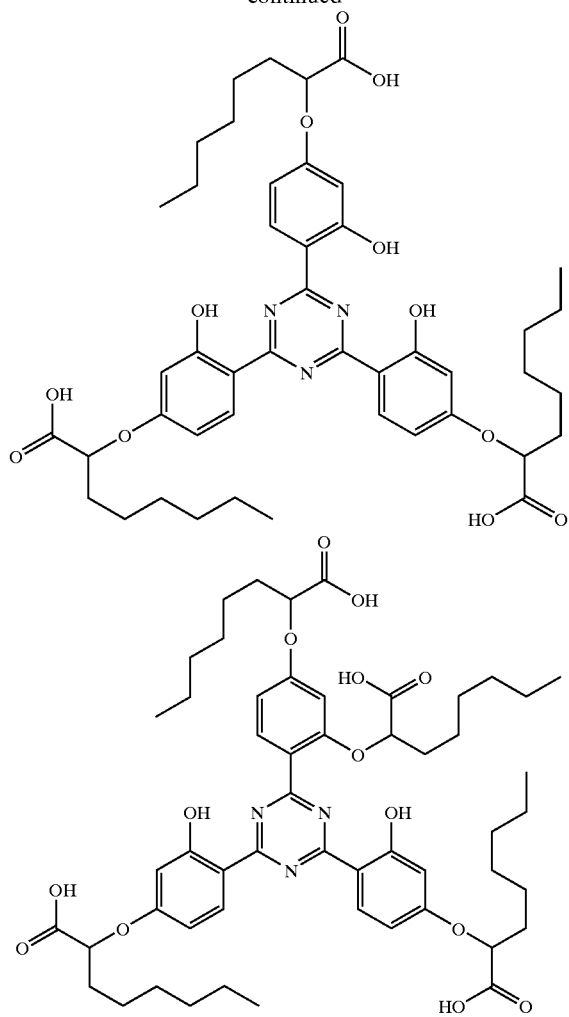

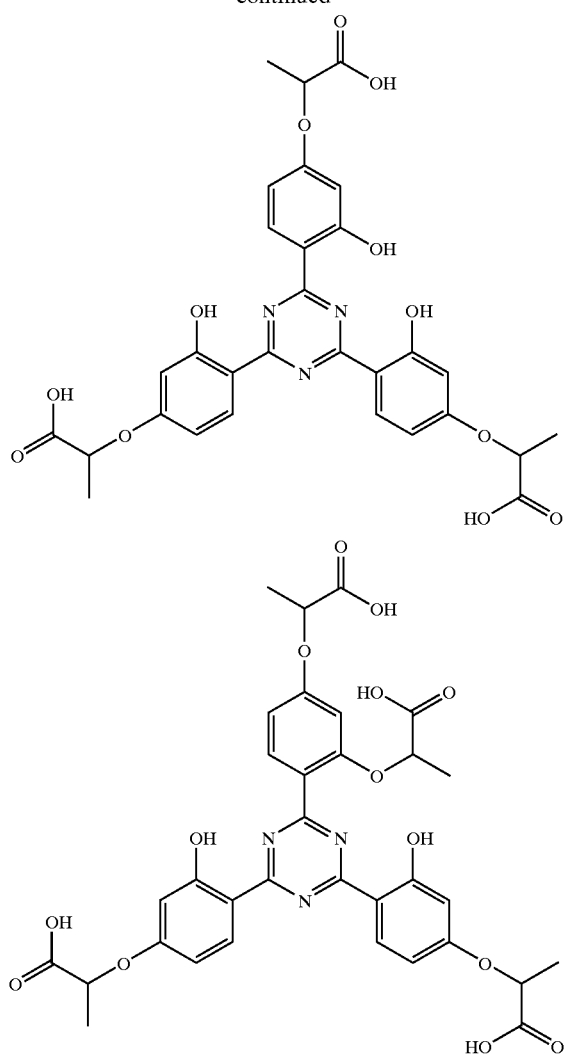

EXAMPLE 8

Working as in Example 5 but starting from the product from Example 4 gives a mixture comprising:

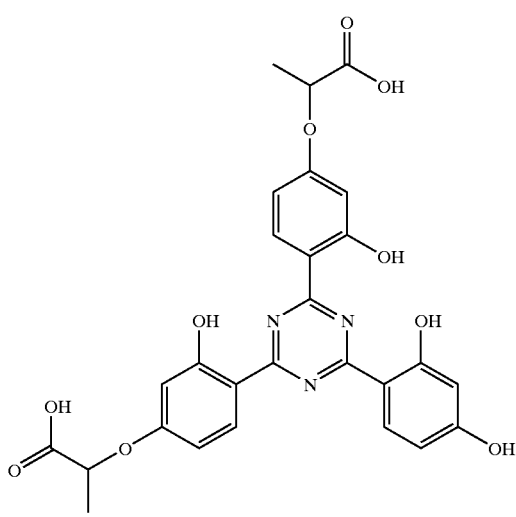

EXAMPLE 9

UV-Absorber Mixture Comprising 2-(2,4-dihydroxyphenyl)-4,6-bis(2-hydroxy-4-(1-potassium-oxycarbonylethoxy)phenyl)-1,3,5-triazine, 2,4,6-tris(2-hydroxy-4-(1-potassium-oxycarbonylethoxy)phenyl)-1,3,5-triazine and 2-(2,4-di(potassium-oxycarbonylethoxy)-phenyl)-4,6-bis(2-hydroxy-4-(1-potassium-oxycarbonylethoxy)phenyl)-1,3,5-triazine 5 g of the mixture of compounds from Example 8 are added to a solution of 1.45 g of KOH in 30 ml of water and the mixture is stirred at room temperature for one hour. It is filtered to give a clear aqueous orange-coloured solution which comprises the following components:

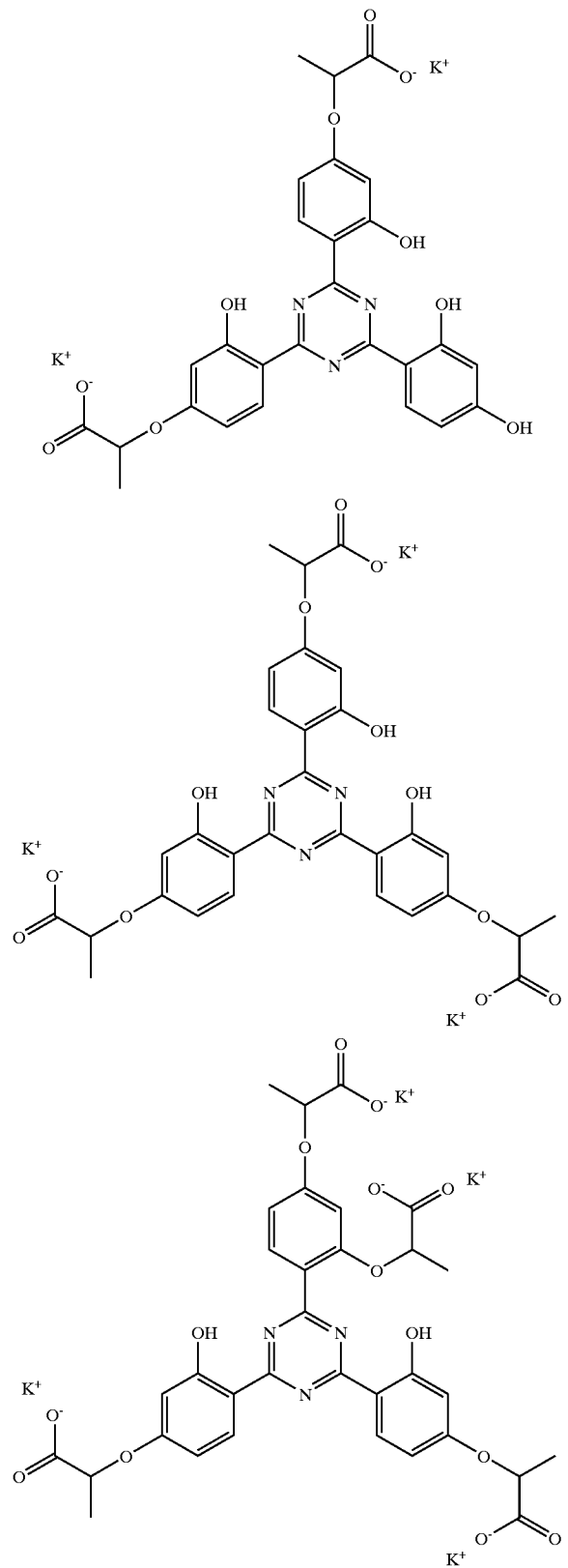
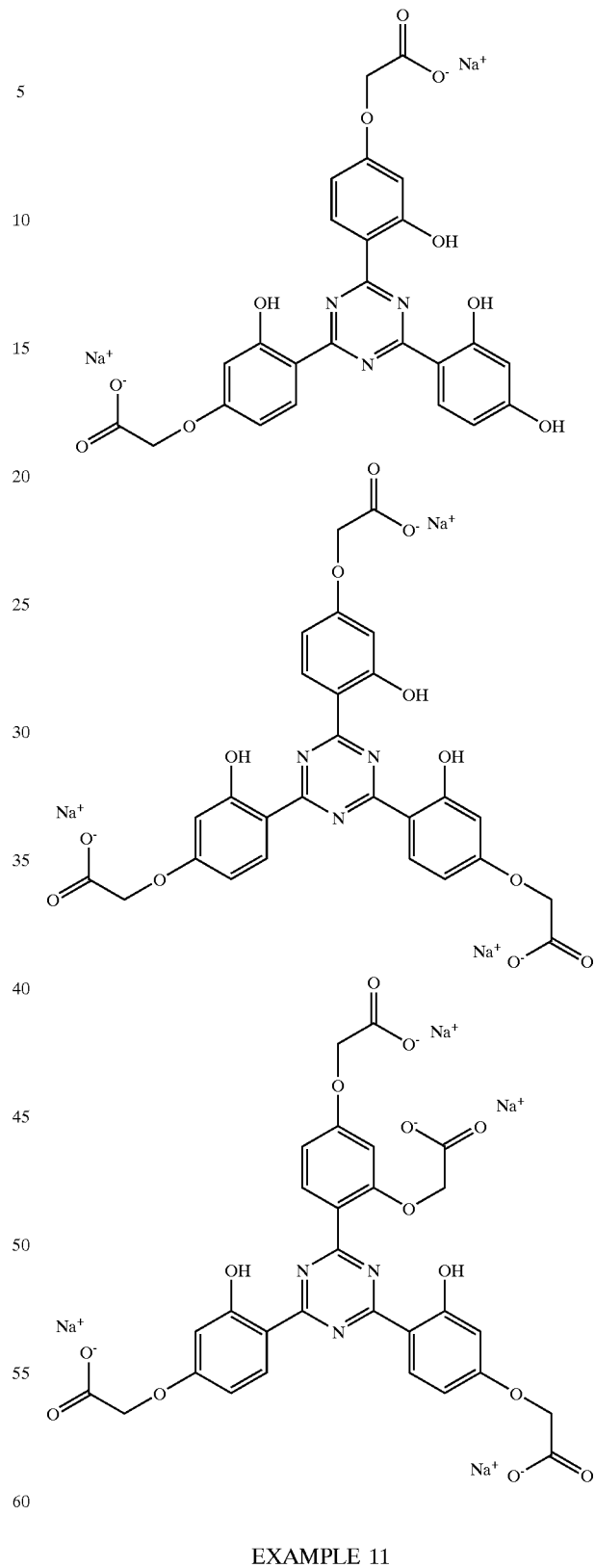
EXAMPLE 10
Working as in Example 9 but starting from the product from Example 6 and with NaOH as base gives a mixture comprising:
EXAMPLE 11
Surface Treatment of Wood
a) Impregnation: 0.5%, relative to the weight of the overall formulation, of the stabilizer of example 4f is added to a commercially available impregnant (Xylamon incolore™; manufacturer: Sepam).

The impregnant is applied by brush to spruce boards (1 application) and dried at room temperature for 24 hours.

--- b) Topcoat: a topcoat is prepared from:

53.48 parts by weight of alkyd resin (Jägalyd Antihydro ™, E. Jäger KG, 60% solution in white spirit);
10.69 parts by weight of a thixotropic auxiliary (Jägalyd Antihydro-Thix ™, E. Jäger KG, 50% solution);
1.92 parts by weight of accelerator (Jäger Antihydro-Trockner ™);
33.44 parts by weight of solvent (Terlitol ™ 30);
0.32 part by weight of anti-skinning agent (Ascinin ™ P, BAYER);
0.15 part by weight of anti-skinning agent (Luactin ™ M, BASF).

---

The topcoat is stabilized by addition of 1.0% of stabilizer of example 4f and 1.0% of the compound in formula T1

(T1)

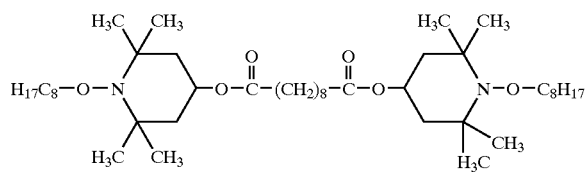

(light stabilizer of the hindered amine type, Ciba Specialty Chemicals), amounts in each case based on the solids content of the binder. A comparative sample is prepared without addition of the abovementioned stabilizers.

The topcoat is applied by brush (3 applications) to the impregnated spruce boards with drying at room temperature for 24 hours after each application.

Subsequently, the samples are subjected to accelerated weathering: UV-A lamps with maximum light intensity at 340 nm; weathering cycle: 5 h light at 58° C., 1 h spraying at 22° C.

After the stated period of weathering, the colour change ΔE is determined in accordance with DIN 6174; the comparison used is an unweathered sample with unstabilized impregnant and unstabilized topcoat. The results show excellent stabilization of the samples stabilized with the mixture of compounds according to Example 4f.

EXAMPLE 11a

A topcoat is prepared as described in Example 11 and applied to pretreated spruce boards, either using no light stabilizer of the hindered amine type or using the compound of the formula Ti. The comparison used is an unstabilized topcoat. The tables below show the results (ΔE in accordance with DIN 6174) after the stated period of weathering. Stated amounts of stabilizer relate in each case to the weight of the solid coating.

Sample a: Accelerated weathering as in Example 11 but permanent light exposure without spraying.

TABLE A

| Colour change ΔE after 1000 h exposure | |
|---|---|
| Additive | ΔE |
| none | 29 |
| 2% comp. from Example 4f | 11 |

Sample b: Accelerated weathering as in Example 11.

TABLE B

| Colour change ΔE after 1200 h accelerated weathering | |
|---|---|
| Additive | ΔE |
| none | 31 |
| 1% comp. from Example 4f + 1% T1 | 23 |

The results show excellent stabilization of the samples stabilized with the mixture of the invention.

EXAMPLE 12

Stabilization of a 2-Coat Metallic Finish

The stabilizer of the invention to be tested is incorporated into 30 g of Solvesso® 100[4)] and tested in a clearcoat of the following composition (parts by weight):

| | |
|---|---|
| Synthacryl ® SC 303[1)] | 27.51 |
| Synthacryl ® SC 370[2)] | 23.34 |
| Maprenal ® 650[3)] | 27.29 |
| Butyl acetate/butanol (37/8) | 4.33 |
| Isobutanol | 4.87 |
| Solvesso ® 150[4)] | 2.72 |
| Kristallöl K-30[5)] | 8.74 |
| Levelling assistant Baysilone ® MA[6)] | 1.2 |
| | 100.00 |

[1)]Acrylic resin, Hoechst AG; 65% solution in xylene/butanol (26/9)

1) Acrylic resin, Hoechst AG; 65% solution in xylene/butanol (26/9)
2) Acrylic resin, Hoechst AG; 75% solution in Solvesso® 100[4)]
3) Melamine resin, Hoechst AG; 55% solution in isobutanol
4) Mixture of aromatic hydrocarbons (manufacturer: Esso); boiling range 182–203° C. (Solvesso® 150) or 161–178° C. (Solvesso® 100)
5) Mixture of aliphatic hydrocarbons (manufacturer Shell); boiling range: 145–200° C.
6) 1% in Solvesso® 150[4)] (manufacturer: Bayer AG)

1.5% by weight of the mixture of compounds from Example 1 or Example 3 or Example 4a in each case are added to the clearcoat; in some samples, an additional 0.7% of the compound

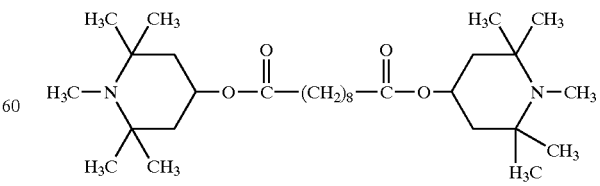

(compound A) is incorporated (amounts in each case based on the solids content of the coating). The comparison used is a clearcoat containing no light stabilizer.

The clearcoat is diluted with Solvesso® 100 to spray viscosity and sprayed onto a prepared aluminium panel (Uniprime® epoxy, silver-metallic basecoat) which is baked at 130° C. for 30 minutes. The result is a dry film thickness of 40–50 µm clearcoat.

The samples are then weathered in an UVCON® weathering apparatus from Atlas Corp. (UVB-313 lamps) with a cycle of 4 h UV exposure at 70° C. and 4 h condensation at 50° C.

The samples are examined at regular intervals for gloss (20" gloss in accordance with DIN 67530) and freedom from cracks. The samples stabilized in accordance with the invention exhibit a markedly better weathering stability (gloss retention, crack resistance) than the unstabilized comparison sample.

EXAMPLE 13

Solubility in Adhesives

To measure the solubility, the compound under test is added to a typical adhesive GELVA® 263 (Solutia; a 44.5% strength solution of a polyacrylate in a mixture of ethyl acetate and hexane, the polyacrylate being a copolymer of methyl methacrylate, 2-ethylhexyl methacrylate and glycidyl methacrylate).

The test compound is dissolved in 5 ml of ethyl acetate, toluene or a mixture of ethyl acetate and toluene. 5 g of GELVA® 263 are admixed to the solution, and 2–3 ml of the resulting solution are introduced into individual glass dishes. The solubility is subsequently determined from the observed crystallization following evaporation of the solvent within a period of a few hours to several weeks.

The solubility data reported in the table below are the observed maximum concentrations at which there is still no sign of onset of crystallization, reported as the overall weight of the admixed triazine compounds to GELVA® 263.

| Compound | Solubility (%) |
|---|---|
| Example 4a | 22.6 |
| Comparison* | 8.0 |

*The comparison used was the single compound 2,4,6-tris(2-hydroxy-4-isooctyloxycarbonylisopropylideneoxyphenyl)-s-triazine (compound no. 4 from GB-A-2337049).

The data show a markedly better solubility in adhesives for the mixture of compounds of the invention than for an Individual compound of similar structure.

EXAMPLE 14

Solar Films

A polyurethane film is produced as follows: 26.2 g of butyl acetate, 5.8 g of ethyl acetate and 0.4 g of 50% FC 430 are admixed to 595 g of acrylic polyol RK 4037 at 75% solids content in methyl amyl ketone (DuPont; MW 7000–9000; OH number 145). 0.75 g of the compound Ti from Example 11 (1% based on the solids content) is added. 0.9 g of Desmodur® N-3390 (aliphatic polyisocyanate, 90% solids content, Bayer) is added to 2.43 g of this mixture. The UV absorber to be tested is incorporated into the acrylic polyol component. The formulation is applied by spincoating to a quartz disk (1000 rpm, 2 seconds). The coating (1.4 mil) is cured at 260° F. for 30 minutes.

UV spectra are recorded using a λ-9 UV-spectrophotometer from Perkin Elmer every 0.5 nm, at 120 mm/min with a gap width of 2 nm.

Loss of UV absorber by weathering is determined by measuring the longwave absorption maximum every 200 h. Extinction at the longwave absorption maximum before the beginning of weathering is about 2.3. Weathering takes place in accordance with SAEJ 1960 (exterior automotive weathering conditions): 0.55 W/m$^2$ at 340 nm using an inner and an outer borosilicate filter; 40 minutes of exposure dry, 20 minutes of exposure wet (front), then 60 minutes of exposure followed by 60 minutes without exposure, in each case with condensation (back); black panel temperature 70° C.; relative atmospheric humidity 50–55% during exposure and 100% during darkness. The results are summarized in the table below; amounts are based on the weight of the overall formulation.

TABLE

Extinction of the polyurethane film before and after 2012 h weathering

| UV Absorber | Extinction before | Extinction after weathering |
|---|---|---|
| 1.6% compound from Example 4a | 2.33 | 1.83 |

The stabilizer of the invention exhibits good persistence in the polyurethane film.

EXAMPLE 15

Application in Photographic Layers

Atop a polyester support, a gelatine layer of the following composition (per m$^2$) is applied in the customary manner:

| Component: | Amount: |
|---|---|
| Gelatine | 1200 mg |
| Tricresyl phosphate | 150 mg |
| Curing agent | 40 mg |
| Wetting agent | 100 mg |
| Compound from Example 4a | 300 mg |

The curing agent used is the potassium salt of 2-hydroxy-4,6-dichloro-1,3,5-triazine, the wetting agent sodium 4,8-diisobutylnaphthalene-2-sulfonate.

The gelatine layer is dried at 20° C. for 7 days.

This gives a clear transparent layer having a maximum optical density of 1.10 which is suitable for a photographic recording material, as a UV filter layer, for example.

Clear layers may be obtained uniformly by halving the amount of tricresyl phosphate or by using dibutyl phthalate instead of tricresyl phosphate.

EXAMPLE 16

The procedure described in Example- 15 is repeated but using a mixture of 1 part by weight of the compound from Example 4a and 1 part by weight of the compound B.

Compound B corresponds to the formula

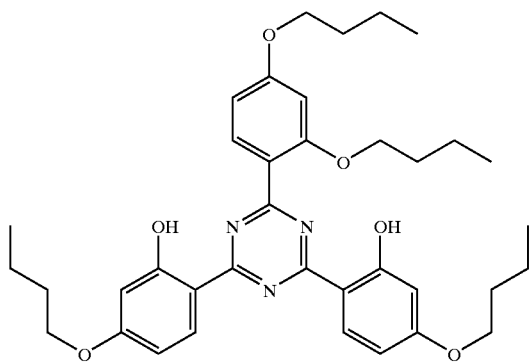

(compound no. 21 from GB-A-2319523).

Clear transparent layers are obtained which are suitable for a photographic recording material, as a UV filter layer, for example.

EXAMPLE 17

Layers are prepared as described in Example 15. The samples are exposed in an Atlas exposure apparatus at 120 kJ/cm$^2$ and the decrease in density at the longwave absorption maximum ($\lambda_{max}$) is determined. The results are summarized in the table below.

| Sample | UVA of the invention | Comparative UVA | Mass ratio | $\lambda_{max}$ | Density decrease |
|---|---|---|---|---|---|
| 3-1 | — | Comp. B | — | 346 nm | 10% |
| 3-2 | Example 4a | — | — | 354 nm | 5% |
| 3-3 | Example 4a | Comp. B | 10/90 | 346 nm | 11% |
| 3-4 | Example 4a | Comp. B | 20/80 | 347 nm | 8% |
| 3-5 | Example 4a | Comp. B | 30/70 | 347 nm | 7% |

A UV filter layer comprising the compound of the invention exhibits outstanding light stability and is therefore suitable for the long-term light protection of photographic layers.

EXAMPLE 18

A photographic material is produced with the following layer construction:

topmost layer
red-sensitive layer
second gelatine interlayer
green-sensitive layer
first gelatine interlayer
blue-sensitive layer
polyethylene base The gelatine layers comprise the following components (per m$^2$ of base material),
Blue-Sensitive Layer
α-(Benzyl-4-ethoxyhydantoin-1-yl)-α-pivaloyl-2-chloro-5-[α-(2,4di-t-amylphenoxy)butanamido]acetanilide (400 mg)
α-(1-Butyl-phenylurazol-4-yl)-α-pivaloyl-5-(3-dodecanesulfonyl-2-methylpropanamido)-2-methoxyacetamide (400 mg)
Dibutyl phthalate (130 mg)
Dinonyl phthalate (130 mg)
Gelatine (1200 mg)
1,5-Dioxa-3-ethyl-3-[β-(3,5-di-t-butyl-4-hydroxyphenyl)-propionyloxymethyl]-8,10-diphenyl-9-thia-[5,5]spiroundecane(150 mg)
Bis(1-acryloyl-2,2,6,6tetramethyl-4piperidyl) 2,2-bis(3,5-di-t-butyl-4-hydroxybenzyl)malonate (150 mg)
3,5-Di-t-butyl-4-hydroxy(2,4-di-t-amylphenyl)benzoate (150 mg)
Poly(N-t-butylacrylamide) (50 mg)
Blue-sensitive silver chlorobromide emulsion (240 mg)
First Gelatine Interlayer
Gelatine (1000 mg)
2-Di-t-octylhydroquinone (100 mg)
Hexyl 5-[2,5-dihydroxy-4-(4-hexyloxycarbonyl-1,1-dimethylbutyl)phenyl]-5-methylhexanoate (100 mg)
Dibutyl phthalate (200 mg)
Diisodecyl phthalate (200 mg)
Green-Sensitive Layer
7-Chloro-2-{2-[2-(2,4-di-t-amylphenoxy)octanamido]-1-methylethyl}-6-methyl-1H-pyrazolo[1,5-b][1,2,4]triazole (100 mg)
6-t-Butyl-7chloro-3-(3-dodecanesulfonylpropyl)-1H-pyrazolo[5,1-o][1,2,4]triazole (100 mg)
Dibutyl phthalate (100 mg)
Dicresyl phosphate (100 mg)
Trioctyl phosphate (100 mg)
Gelatine (1400 mg)
3,3,3',3'-Tetramethyl-5,5',6,6'-tetrapropoxy-1,1'-spirobiindane (100 mg)
4-(i-Tridecyloxyphenyl)thiomorpholine 1,1-dioxide (100 mg)
4,4'-Butylidenebis(3-methyl-6t-butylphenol) (50 mg)
2,2'-Isobutylidenebis(4,6-dimethylphenol) (10 mg)
3,5-Dichloro-4-(hexadecyloxycarbonyloxy)ethylbenzoate (20 mg)
3,5-Bis[3-(2,4-di-t-amylphenoxy)propylcarbamoyl]sodium benzenesulfonate (20 mg)
Green-sensitive silver chlorobromide emulsion (150 mg)
Second Gelatine Interlayer
Gelatine (1000 mg)
5-Chloro-2-(3,5-di-tbutyl-2-hydroxyphenyl)benzo-1,2,3-triazole (200 mg)
2-(3-Dodecyl-2-hydroxy-5-methylphenyl)benzo-1,2,3-triazole (200 mg)
Trinonyl phosphate (300 mg)
2,5-Di-t-octylhydroquinone (50 mg)
Hexyl 5-[2,5-dihydroxy-4-(4-hexyloxycarbonyl-1,1-dimethylbutyl)phenyl]-5-methylhexanoate (50 mg)
Red-Sensitive Layer
2-[a-(2,4-Di-t-amylphenoxy)butanamido]-4,6-di-chloro-5-ethylphenol (150 mg)
2,4-Dichloro-3-ethyl-6-hexadecanamidophenol (150 mg)
4-Chloro-2-(1,2,3,4,5-pentafluorobenzamido)-5-[2-(2,4-di-t-amylphenoxy)-3 methylbutanamido]phenol (100 mg)
Dioctyl phthalate (100 mg)
Dicyclohexyl phthalate (100 mg)
Gelatine (1200 mg)
5-Chloro-2-(3,5-di-t-butyl-2-hydroxyphenyl)benzo-1,2,3-triazole (100 mg)
2-(3-Dodecyl-2-hydroxy-5-methylphenyl)benzo-1,2,3-triazole (100 mg)
3,5-Di-t-butyl-4-hydroxy(2,4-di-t-amylphenyl)benzoate (50 mg)
Poly(N-t-butylacrylamide) (300 mg)
N,N-Diethyl-2,4-di-t-amylphenoxyacetamide (100 mg)

2,5-Di-t-octylhydroquinone (50 mg)
Red-sensitive silver chlorobromide emulsion (200 mg)

The topmost layer is prepared with and without UV absorber;

With UV Absorber:

2,5-Di-t octylhydroquinone (20 mg)
Hexyl 5-[2,5-dihydroxy-4-(4-hexyloxycarbonyl-1,1-dimethylbutyl)phenyl]-5-methylhexanoate (20 mg)
Gelatine (400 mg)
Trinonyl phosphate (120 mg)
UV absorber compound from Example 4a (200 mg)

Without UV Absorber:

Gelatine (800 mg)

The curing agent used is 2,4-dichloro-6-hydroxytriazine K salt solution, the wetting agent the sodium salt of diisobutylnaphthalenesulfonic acid.

Exposed onto the samples (with blue, green or red light respectively) are in each case three step wedges with a density difference of 0.3 log E per stage. Subsequently, the samples are processed in accordance with process RA-4 (Kodak) for colour papers.

Following exposure and processing, the remission densities are measured in the red for the cyan stage, in the green for the magenta stage and in the blue for the yellow stage, at a density between 0.9 and 1.1 of the wedges. The wedges are then exposed with a total of 15 kJ/cm² in an Atlas exposure apparatus and the remission densities are measured again.

With the magenta wedge, additionally, the remission density is measured in the blue before and after exposure, for the yellowing.

The presence of the compound of the invention in the topmost layer reduces the dye density loss of the cyan, magenta and yellow image dye and also the yellowing of the magenta layer.

EXAMPLE 19

Light Stabilization of Printing Inks

An ink-jet printing ink is prepared by mixing together the following components:

2 g of Acid Red 52

20 g of diethylene glycol 78 g of water.

The ink is stirred until all of the components have dissolved and the solution is then filtered through a Millipore filter with a pore size of 0.45 mm.

One portion of the ink is inserted into an emptied and cleaned cartridge of an HP DeskJet 510 printer. A printed sample is produced on paper from the company sihl+eika (ref. 193.178) (sample 1, comparison).

The compound of the invention (mixture) from Example 9 is tested by mixing 0.30 g of this compound with 2.70 g of the ink described above and using this mixture to produce a printed sample as described before (sample 2).

After drying, the colour density of the two sample prints are determined with a densitometer (Macbeth TR 924) using a status A filter. Subsequently, the sample prints are exposed in an Atlas Ci 35 weathers-o-meter with an 81 klux xenon lamp through a 6 mm thick window glass filter (dose: 3660 klux h). Following exposure, the colour density is measured again in order to determine the percentage loss of colour density. The results are shown in the table below:

| Sample | Additive | Colour density loss after 3660 klux h (%) |
|---|---|---|
| 1 (Comparison) | — | 46 |
| 2 (Invention) | Ex. 9 | 26 |

As the table shows the mixture of compounds of the invention significantly improves the light stability of the dye.

What is claimed is:

1. A mixture of compounds comprising compounds $G_2$, $G_3$ and $G_4$ and optionally, at least one further compound selected from the group consisting of $G_0$, $G_1$, $G_3$, $G_4$, $G_5$ and $G_6$, wherein $G_2$, $G_3$ and $G_4$ are each present from 5–80 parts by weight, based on 100 parts by weight of the total of compounds $G_0$–$G_6$, and where the compounds $G_0$–$G_6$ each correspond to the formula I

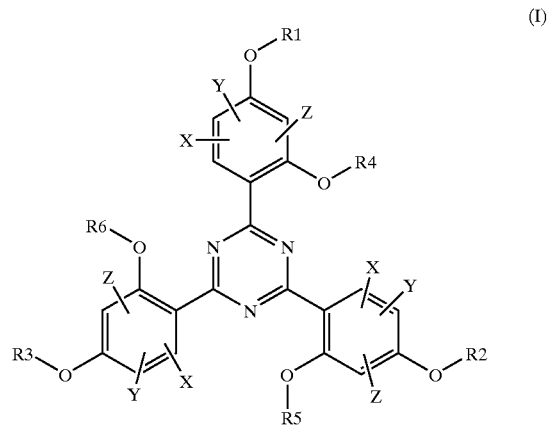

(I)

in which

X, Y and Z independently of one another are H, $T_1$, $OT_1$, $NT_1T_2$, $ST_1$, $SOT_1$, $SO_2T_1$, $SO_2NT_1T_2$, $SO_3H$, $SO_3T_1$, $SO_3M$ or —D; where $T_1$ and $T_2$ are $C_1$–$C_{50}$alkyl, $C_5$–$C_{12}$cycloalkyl, $C_7$–$C_{18}$arylalkyl, $C_7$–$C_{18}$alkylaryl, $C_6$–$C_{18}$aryl, $C_2$–$C_{50}$alkenyl, $C_5$–$C_{12}$cycloalkenyl, $C_2$–$C_{50}$alkynyl, $C_5$$C_{12}$cycloalkynyl, $C_5$–$C_{18}$bicycloalkyl, $C_6$–$C_{18}$bicycloalkenyl; or one of these radicals substituted by one or more D and/or, if desired, interrupted by one or more units E;

D is selected from the group consisting of —R, —OH, —OR, —SR, —NRR', —NRSO₂R', —SOR, —SO₂R, —SO₂NRR', —SO₃H, —SO₃M, —SO₃R, oxiranyl, -Hal, —CN, —COR, —COOR, —COOM, —CONRR', —OCOR, —OCOOR, —OCONRR', —NRCOR', —NRCOOR', and —NRCONR'R";

E is selected from the group consisting of —O—, —S—, —NR—, —SO—, —SO₂—, —SO₂NR—, —CO—, —COO—, —CONR—, —OCO—, —O—CO—O—, OCONR—, —NRCO—, —NR—CO—O— and —NRCONR'—;

R, R', R", R* independently of one another are H, $C_1$–$C_{50}$alkyl, $C_5$–$C_{12}$cycloalkyl, $C_7$–$C_{18}$arylalkyl, $C_7$–$C_{18}$alkylaryl, $C_6$–$C_{18}$aryl, $C_2$–$C_{50}$alkenyl, $C_5$–$C_{12}$cycloalkenyl, $C_2$–$C_{50}$alkynyl,

53

$C_5$–$C_{12}$cycloalkynyl, $C_5$–$C_{18}$bicycloalkyl or $C_6$–$C_{18}$bicycloalkenyl; or are one of these aforementioned hydrocarbon radicals substituted by OH and/or interrupted by O;

Hal is —F, —Cl, —Br or —I;

M is a monovalent metal cation or is N(RR'R"R*)$^+$ or is P(RR'R"R*)$^+$;

and in which, in the compound $G_0$, the radicals $R_1$, $R_2$, $R_3$, $R_4$, $R_5$ and $R_6$ are each hydrogen;

$G_1$, one radical from the group $R_1$, $R_2$, $R_3$, $R_4$, $R_5$ and $R_6$ is Q and the others are each hydrogen;

$G_2$, two radicals from the group $R_1$, $R_2$, $R_3$, $R_4$, $R_5$ and $R_6$ are each Q and the others are each hydrogen;

$G_3$, three radicals from the group $R_1$, $R_2$, $R_3$, $R_4$, $R_5$ and $R_6$ are each Q and the others are each hydrogen;

$G_4$, four radicals from the group $R_1$, $R_2$, $R_3$, $R_4$, $R_5$ and $R_6$ are each Q and the others are each hydrogen;

$G_5$, five radicals from the group $R_1$, $R_2$, $R_3$, $R_4$, $R_5$ and $R_6$ are each Q and 1 radical is hydrogen;

$G_6$, the radicals $R_1$, $R_2$, $R_3$, $R_4$, $R_5$ and $R_6$ are each Q; and

Q is —$T_1$, —$COT_1$, —COH, —$COOT_1$, —$CONHT_1$, —$CONH_2$ or —$CONT_1T_2$.

2. A compound mixture according to claim 1, comprising $G_2$ and a further compound from the group $G_0$, $G_1$, $G_3$, $G_4$, $G_5$, $G_6$ in each case in an amount of from 1 to 99 parts by weight per 100 parts by weight of the total compounds $G_0$–$G_6$ present in the stabilizer mixture.

3. A compound mixture according to claim 1, comprising $G_2$ and also $G_3$ and/or $G_4$ in each case in an amount of from 1 to 98 parts by weight per 100 parts by weight of the total compounds $G_0$–$G_6$ present in the mixture.

4. A compound mixture according to claim 1, in which, in the compounds $G_1$–$G_6$ of the formula I, X, Y and Z independently of one another are —H, —$T_1$, or D;

$T_1$ and $T_2$ independently of one another are $C_1$–$C_{18}$alkyl, $C_5$–$C_{12}$cycloalkyl, $C_7$–$C_{18}$phenylalkyl, $C_7$–$C_{18}$alkylphenyl, phenyl, naphthyl, biphenylyl, $C_2$–$C_{18}$alkenyl, $C_5$–$C_{12}$cycloalkenyl, $C_2$–$C_{12}$-alkynyl; or are $C_1$–$C_{18}$alkyl, $C_5$–$C_{12}$cycloalkyl, $C$-$_7C_{18}$phenylalkyl, $C_7$–$C_{18}$alkylphenyl, phenyl, naphthyl, biphenylyl, $C_2$–$C_{18}$alkenyl, $C_5$–$C_{12}$cycloalkenyl, $C_2$–$C_{12}$alkynyl in each case substituted by one or more D; or are $C_2$–$C_{50}$alkyl, $C_7$–$C_{18}$phenylalkyl, $C_7$–$C_{18}$alkylphenyl, $C_5$–$C_{12}$-cycloalkyl, $C_5$–$C_{12}$cycloalkenyl or $C_4$–$C_{18}$alkenyl in each case interrupted by one or more E; or are $C_2$–$C_{50}$alkyl, $C_3$–$C_{18}$alkenyl, $C_7$–$C_{18}$alkylphenyl, $C_5$–$C_{12}$cycloalkyl, $C_5$–$C_{12}$cycloalkenyl or $C_7$–$C_{18}$phenylalkyl which are substituted by D and interrupted by E;

D is —R, —OH, —OR, —NRR', -Hal, —CN, —COR, —COOR, —COOM, —CONRR', —OCOR, —OCOOR, —OCONRR', —NRCOR', —NRCOOR', —NRCONR'R", oxiranyl, —SO$_3$H, —SO$_3$M;

E is —O—, —NR—, —CO—, —COO—, —CONR—, —OCO—, —OCOO—, OCONR—, —NRCO—, —NRCOO—, —NRCONR'—;

R, R', R", R* independently of one another are H, $C_1$–$C_{50}$alkyl, $C_5$–$C_{12}$cycloalkyl, $C_7$–$C_{18}$-phenylalkyl, $C_7$–$C_{18}$alkylphenyl, phenyl, naphthyl, biphenylyl, $C_2$–$C_{50}$alkenyl, $C_5$–$C_{12}$-cycloalkenyl, $C_2$–$C_{50}$alkynyl;

54

Hal is —F or —Cl; and

M is an alkali metal cation or N(RR'R"R*)$^+$.

5. A compound mixture according to claim 1, in which, in the compounds $G_1$–$G_6$ of the formula I, Q is —$T_1$, —$COT_1$ or —$CONT_1T_2$;

X, Y and Z independently of one another are —H, —$T_1$, D;

D is —R, —OH, —OR, -Hal, —COR, —COOR, —COOM, —CONRR', —OCOR, —OCOOR, —OCONRR', —SO$_3$H, —SO$_3$M;

E is —O—, —CO—, —COO—, —CONR—, —OCO—, —OCOO—, OCONR—;

R, R', R" independently of one another are H, $C_1$–$C_{18}$alkyl, cyclohexyl, cyclododecyl, $C_7$–$C_{18}$-phenylalkyl, $C_7$–$C_{18}$alkylphenyl, phenyl, $C_2$–$C_{12}$alkenyl; and Hal is —F or —Cl; and M is Li, Na or K.

6. A compound mixture according to claim 1, in which, in the compounds $G_1$–$G_6$ of the formula I, Q is —$T_1$, —$COT_1$, —$CONT_1T_2$;

X, Y and Z independently of one another are —H, —$T_1$ or —D;

$T_1$ and $T_2$ independently of one another are $C_1$–$C_{18}$alkyl, $C_5$–$C_{12}$cycloalkyl, $C_7$–$C_{18}$phenylalkyl, $C_7$–$C_{18}$alkylphenyl, phenyl, naphthyl, biphenylyl, $C_2$–$C_{18}$alkenyl; or are $C_1$–$C_{18}$alkyl, cyclohexyl, $C_7$–$C_{18}$phenylalkyl, $C_7$–$C_{18}$alkylphenyl, phenyl, $C_3$–$C_{12}$alkenyl in each case substituted by D; or are $C_3$–$C_{50}$alkyl, $C_7$–$C_{18}$phenylalkyl, $C_7$–$C_{18}$alkylphenyl or $C_4$–$C_{18}$alkenyl interrupted by E; or are $C_2$–$C_{50}$alkyl or $C_4$–$C_{18}$alkenyl or $C_7$–$C_{18}$phenylalkyl which are substituted by D and interrupted by E;

D is —R, —OH, —OR, -Hal, —COR", —COOR, —COOM, —OCOR", —SO$_3$H, —SO$_3$M;

E is —O—, —CO—, —COO—, —OCO—;

R is H, $C_1$–$C_{18}$alkyl, cyclohexyl, $C_7$–$C_{18}$phenylalkyl, $C_7$–$C_{18}$alkylphenyl, phenyl, $C_3$–$C_{12}$alkenyl;

R" is H, $C_1$–$C_{18}$alkyl, cyclohexyl, $C_7$–$C_{18}$phenylalkyl, $C_7$–$C_{18}$alkylphenyl, phenyl, $C_3$–$C_{12}$alkenyl;

Hal is —F or —Cl; and

M is Li, Na or K.

7. A composition comprising

A) an organic material sensitive to damage by light, oxygen and/or heat, and

B) as a stabilizer, a mixture of compounds according to claim 1.

8. A composition according to claim 7, comprising from 0.01 to 15 parts by weight of component B per 100 parts by weight of component A.

9. A composition according to claim 7, wherein component A is a thermoplastic polymer or a binder for coatings or a reprographic material or wood or wood-containing material.

10. A composition according to claim 7, further comprising an additive selected from the group consisting of the antioxidants, UV absorbers and light stabilizers, metal deactivators, phosphites and phosphonites, hydroxylamines, nitrones, thiosynergists, peroxide destroying compounds, polyamide stabilizers, basic costabilizers, nucleating agents, fillers and reinforcing agents, plasticizers, lubricants, emulsifiers, dispersants, pigments, rheological additives, catalysts, levelling assistants, optical brighteners, flame retardants, antistats, blowing agents, benzofuranones and indolinones.

11. A composition according to claim 7, further comprising one or more stabilizers selected from the group consisting of the sterically hindered amines, 2-(2-hydroxyphenyl)-1,3,5-triazines, 2-hydroxyphenyl-2H-benzotriazoles, 2-hydroxybenzophenones and oxalanilides.

12. A method of stabilizing organic material with respect to damaging exposure to light, oxygen and/or heat, which comprises admixing and/or applying to said material as stabilizer a mixture of compounds according to claim 1.

13. A method of stabilizing organic material with respect to damaging exposure to light, oxygen and/or heat, which comprises admixing and/or applying to said material as stabilizer a compound $G_2$, $G_3$, $G_4$, $G_5$ or $G_6$ of the formula III

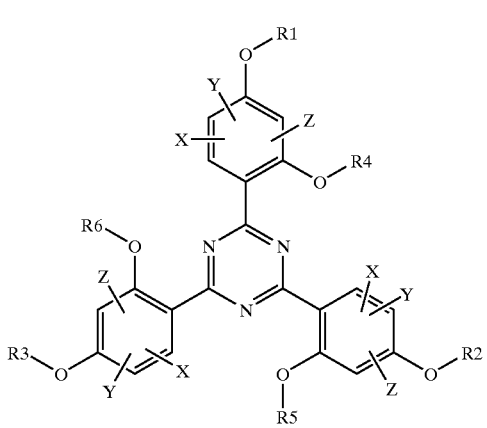

in which

X, Y and Z independently of one another are H, $T_1$, $OT_1$, $NT_1T_2$, $ST_1$, $SOT_1$, $SO_2T_1$, $SO_2NT_1T_2$, $SO_3H$ $SO_3T_1$, $SO_3M$ or —D; where $T_1$ and $T_2$ are $C_1$–$C_{50}$alkyl, $C_5$–$C_{12}$cycloalkyl, $C_7$–$C_{18}$arylalkyl, $C_7$–$C_{18}$alkylaryl, $C_6$–$C_{18}$aryl, $C_2$–$C_{50}$alkenyl, $C_5$–$C_{12}$cycloalkenyl, $C_2$–$C_{50}$alkynyl, $C_5$–$C_{12}$cycloalkynyl, $C_5$–$C_{18}$bicycloalkyl, $C_6$–$C_{18}$bicycloalkenyl; or one of these radicals substituted by one or more D and/or, if desired, interupted by one or more units E;

$T_3$ is $C_1$–$C_{50}$alkyl, $C_2$–$C_{50}$alkenyl, $C_2C_{50}$alkynyl; or $C_1$–$C_{50}$alkyl $C_5$–$C_{12}$cycloalkyl, $C_7$–$C_{18}$arylalkyl, $C_7$–$C_{18}$alkylaryl, $C_6$–$C_{18}$aryl, $C_2$–$C_{50}$alkenyl, $C_5$–$C_{12}$cycloalkenyl, $C_2$–$C_{50}$alkynyl, $C_5$–$C_{12}$cycloalkynyl, $C_5$–$C_{18}$bicycloalkyl, $C_6$–$C_{18}$bicycloalkenyl in each case substituted by one or more —SOR, —SO$_2$R, —SO$_2$NRR', —SO$_3$H, —SO$_3$M, —COR, —COOR, —COOM, —CONRR', —OCOR, —OCOOR, —OCONRR', —NRCOR', —NRCOOR', —NRCONR'R";

$T_4$ is $C_1$–$C_{50}$alkyl, $C_5$–$C_{12}$cycloalkyl, $C_7$–$C_{18}$arylalkyl, $C_7$–$C_{18}$alkylaryl, $C_6$–$C_{18}$aryl, $C_2$–$C_{50}$alkenyl, $C_5$–$C_{12}$cycloalkenyl, $C_2$–$C_{50}$alkynyl, $C_5$–$C_{12}$cycloalkynyl, $C_5$–$C_{18}$bicycloalkyl, $C_6$–$C_{18}$bicycloalkenyl in each case substituted by one or more —COOM and, if desired, interrupted by one or more units E;

D is selected from the group consisting of —R, —OH, —OR —SR, —NRR', —NRSO$_2$R', —SOR, —SO$_2$R, —SO$_2$NRR', —SO$_3$H, —SO$_3$M, -Hal, —CN, —COR, —COOR, —COOM, —CONRR', —OCOR, —OCOOR, —OCONRR', —NRCOR', —NRCOOR' and —NRCONR'R";

E is selected from the group consisting of —O—, —S—, —NR—, —SO—, —SO$_2$—, —SO$_2$NR—, —CO—, —COO—, —CONR—, —OCO—, —O—COO—, OCONR—, —NRCO—, —NR—CO—O— and —NRCONR'—;

R, R', R" independently of one another are H, $C_1$–$C_{50}$alkyl, $C_5$–$C_{12}$cycloalkyl, $C_7$–$C_{18}$arylalkyl, $C_7$–$C_{18}$alkylaryl, $C_6$–$C_{18}$aryl, $C_1$–$C_{50}$alkenyl, $C_5$–$C_{12}$cycloalkenyl, $C_2$–$C_{50}$alkynyl, $C_5$–$C_{12}$cycloalkynyl, $C_5$–$C_{18}$bicycloalkyl or $C_6$–$C_{18}$bicycloalkenyl:

Hal is —F, —Cl, —Br or —I;

M is a monovalent metal cation or $N(R)_4^+$ or $P(R)_4^+$;

and in which, in the compound $G_1$, the radical $R_1$ is $Q_1$ and $R_2$, $R_3$, $R_4$, $R_5$ and $R_6$ are each hydrogen:

$G_2$, the radicals $R_1$ and $R_2$ independently of one another are each $Q_2$ and $R_3$, $R_4$, $R_5$ and $R_6$ are each hydrogen:

$G_3$, the radicals $R_1$, $R_2$, and $R_3$ independently of one another are each $Q_3$ and $R_4$, $R_5$ and $R_6$ are each hydrogen;

$G_4$, the radicals $R_1$, $R_2$, $R_3$ and $R_4$ independently of one another are each $Q_3$ and $R_5$ and $R_6$ are each hydrogen;

$G_5$, the radicals $R_1$ $R_2$, $R_3$, $R_4$ and $R_5$ independently of one another are each $Q_3$ and $R_6$ is hydrogen;

$G_6$, the radicals $R_1$, $R_2$, $R_3$ $R_4$, $R_5$ and $R_6$ independently of one another are each $Q_3$; and $Q_1$ is —$T_1$, —$COT_1$, —COH, —$COOT_1$, or —$CONT_1T_2$; and $Q_2$, is —$T_3$, —$COT_1$, —COH, —$COOT_1$ or —$CONT_1T_2$; and $Q_3$ is —$T_4$.

* * * * *